US009027387B2

(12) United States Patent
Blackburn et al.

(10) Patent No.: US 9,027,387 B2
(45) Date of Patent: May 12, 2015

(54) MULTIFUNCTIONAL POTENTIOMETRIC GAS SENSOR ARRAY WITH AN INTEGRATED TEMPERATURE CONTROL AND TEMPERATURE SENSORS

(75) Inventors: Bryan M. Blackburn, Gainesville, FL (US); Eric D. Wachsman, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 601 days.

(21) Appl. No.: 12/682,365

(22) PCT Filed: Oct. 9, 2008

(86) PCT No.: PCT/US2008/079416
§ 371 (c)(1),
(2), (4) Date: May 25, 2010

(87) PCT Pub. No.: WO2009/049091
PCT Pub. Date: Apr. 16, 2009

(65) Prior Publication Data
US 2010/0264900 A1 Oct. 21, 2010

Related U.S. Application Data

(60) Provisional application No. 60/978,696, filed on Oct. 9, 2007.

(51) Int. Cl.
*G01N 7/00* (2006.01)
*G01N 27/406* (2006.01)
*G01N 27/407* (2006.01)

(52) U.S. Cl.
CPC ........ *G01N 27/4067* (2013.01); *G01N 27/4075* (2013.01)

(58) Field of Classification Search
USPC .................... 73/31.05, 31.06; 324/71.1, 71.5; 340/632; 204/424–429; 205/781, 205/783.5, 784, 784.5, 785; 422/83, 88, 90, 422/98
See application file for complete search history.

(56) References Cited

U.S. PATENT DOCUMENTS 5,389,218 A 2/1995 Bonne et al.
5,389,225 A 2/1995 Aagard et al.
(Continued)

FOREIGN PATENT DOCUMENTS

DE 44 08 504 9/1995
JP 11-287785 10/1999
(Continued)

OTHER PUBLICATIONS

Wachsman, E.D., "Multifunctional (NOx/CO/O2) Solid-State Sensors for Coal Combustion Control," *Information Bridge: Department of Energy Scientific and Technical Information*, May 29, 2005.
(Continued)

*Primary Examiner* — Peter Macchiarolo
*Assistant Examiner* — Nathaniel Kolb
(74) *Attorney, Agent, or Firm* — Saliwanchik, Lloyd & Eisenschenk

(57) ABSTRACT

Embodiments of the subject invention relate to a gas sensor and method for sensing one or more gases. An embodiment incorporates an array of sensing electrodes maintained at similar or different temperatures, such that the sensitivity and species selectivity of the device can be fine tuned between different pairs of sensing electrodes. A specific embodiment pertains to a gas sensor array for monitoring combustion exhausts and/or chemical reaction byproducts. An embodiment of the subject device related to this invention operates at high temperatures and can withstand harsh chemical environments. Embodiments of the device are made on a single substrate. The devices can also be made on individual substrates and monitored individually as if they were part of an array on a single substrate. The device can incorporate sensing electrodes in the same environment, which allows the electrodes to be coplanar and, thus, keep manufacturing costs low. Embodiments of the device can provide improvements to sensitivity, selectivity, and signal interference via surface temperature control.

54 Claims, 28 Drawing Sheets

(56) References Cited

U.S. PATENT DOCUMENTS

| | | | |
|---|---|---|---|
| 5,397,442 A | | 3/1995 | Wachsman |
| 5,429,727 A | * | 7/1995 | Vogt et al. .................. 205/779.5 |
| 5,591,896 A | * | 1/1997 | Lin .............................. 73/31.05 |
| 5,643,429 A | | 7/1997 | Wachsman |
| 5,788,833 A | | 8/1998 | Lewis et al. |
| 5,889,196 A | * | 3/1999 | Ueno et al. ................... 73/23.31 |
| 6,551,497 B1 | * | 4/2003 | Gao et al. ....................... 205/781 |
| 6,598,596 B2 | | 7/2003 | Wachsman et al. |
| 6,635,161 B2 | * | 10/2003 | Inagaki ......................... 204/425 |
| 6,660,231 B2 | | 12/2003 | Moseley |
| 7,037,415 B2 | * | 5/2006 | Cramer et al. ................ 204/429 |
| 2005/0214170 A1 | | 9/2005 | Kading |
| 2005/0241368 A1 | * | 11/2005 | Yamauchi et al. ........... 73/31.05 |
| 2006/0070890 A1 | | 4/2006 | Itoh |
| 2006/0171847 A1 | * | 8/2006 | Morris ............................ 422/83 |
| 2007/0012566 A1 | | 1/2007 | Nair et al. |
| 2007/0080075 A1 | * | 4/2007 | Wang et al. ................... 205/781 |

FOREIGN PATENT DOCUMENTS

| | | |
|---|---|---|
| JP | 2000-206089 | 7/2000 |
| JP | 2005-504961 | 2/2005 |
| JP | 2006-098136 | 4/2006 |
| JP | 2007-327933 | 12/2007 |
| WO | WO 97/42495 | 11/1997 |
| WO | WO-03/027658 | 4/2003 |

OTHER PUBLICATIONS

Blackburn, B.M., et al., "Multifunctional Gas Sensor Array with Improved Selectivity Through Local Thermal Modification," 212th Electrochemical Society Meeting, Oct. 7-12, 2007, Washington, D.C., Abstract No. 797.

Blackburn, B.M., et al., "Multifunctional Gas Sensor Array with Improved Selectivity Through Local Thermal Modification," *ECS Transactions*, 2008, pp. 141-153, vol. 11, No. 33.

Blackburn, B.M., et al., "Multifunctional Potentiometric Gas Sensor Array with an Integrated Heater and Temperature Sensors," *Advances in Electronic Ceramics*, 2008, The American Ceramic Society, C. Randall et al.(ed.), pp. 101-108.

\* cited by examiner

MULTIFUNCTIONAL POTENTIOMETRIC GAS SENSOR ARRAY WITH AN INTEGRATED TEMPERATURE CONTROL AND TEMPERATURE SENSORS

CROSS-REFERENCE TO RELATED APPLICATIONS

The present application is the U.S. National Stage Application of International Patent Application No. PCT/US2008/079416, filed on Oct. 9, 2008, which claims the benefit of U.S. Provisional Application Ser. No. 60/978,696, filed Oct. 9, 2007, both of which are hereby incorporated by reference herein in their entirety, including any figures, tables, or drawings.

The subject invention was made with government support under a research project supported by the Department of Energy, Contract Nos. DE-FG26-02NT41533 and DE-FC26-03NT41614. The government has certain rights to this invention.

BACKGROUND OF INVENTION

Potentiometric gas sensors based on measuring the potential difference between a semiconducting metal oxide and a noble metal pseudo-reference electrode in the same gas environment offer highly selective devices that are easily manufactured and can withstand harsh environments without degrading performance. Furthermore, they are insensitive to large swings in $O_2$ concentration, such as those that occur in a combustion exhaust. Such solid-state potentiometric gas sensors show great promise for detecting pollutants such as $NO_x$, CO, and hydrocarbons from ppb to ppm level concentrations for exhaust monitoring. They also may be used in other applications such as in the biomedical field for breath analysis.

Potentiometric gas sensors have an output voltage signal that can be measured in many different ways and can be used to determine individual gas concentration(s) in a gas mixture or that of a varying concentration of single species in the absence of other gases. The voltage difference between two electrodes, which make up an "electrode-pair", can be monitored as the potential at one or each electrode changes.

Potentiometric gas sensors are utilized by measuring the output voltage signal that can be used to determine individual gas concentration(s) in a gas mixture or that of a varying concentration of single species in the absence of other gases.

Solid-state potentiometric gas sensors with semiconducting metal oxide electrodes (such as p-type $La_2CuO_4$ (LCO)) have shown much promise for the monitoring of pollutant gas (such as $NO_x$) levels in combustion exhaust. They are sensitive to ppm levels of $NO_x$ and concentrations. However, the selectivity and cross-sensitivity of these sensors is currently inadequate for commercial application. A prime example of this is the inability to discriminate between NO and $NO_2$ (the primary components of $NO_x$). It is often important to know the concentration of each of these individual gases; however, most $NO_x$ sensors cannot determine which of these species is present or determine their absolute concentration in mixed gas streams. In fact, poor selectivity hinders most solid-state pollutant sensors. Currently available devices for monitoring combustion exhausts and/or reaction byproducts are limited in several ways. Current devices detect only one gas species or detect multiple species only by utilizing expensive electronics to extrapolate the gas concentrations from the measurement or to take the measurement. Current devices can require an air reference, which complicates the design, and/or have complicated manufacturing steps that increase cost.

A reference electrode is typically used to compare the changing EMF of a sensing electrode to an EMF that does not change (i.e., a reference state). A pseudo-reference is an electrode which can be used to compare all other sensing electrodes in a single gas environment. However, the pseudo-reference has an EMF that changes at the same time that the sensing electrodes are changing. Accordingly, a pseudo-reference does not actually represent a true reference state.

BRIEF SUMMARY

Embodiments of the subject invention relate to a gas sensor and method for sensing on or more gases specific embodiments pertain to a potentiometric gas sensor and method for sensing on or more gases. Additional embodiments are directed to amperometric and/or impedimetric gas sensors and method for sensing one or more gases. An embodiment incorporates an array of sensing electrodes maintained at similar or different temperatures, such that the sensitivity and species selectivity of the device can be fine tuned between different pairs of sensing electrodes. A specific embodiment pertains to a gas sensor array for monitoring combustion exhausts and/or reaction byproducts. An embodiment of the subject device related to this invention operates at high temperatures and can withstand harsh chemical environments.

Embodiments of the device are made on a single substrate. In other embodiments, several different single electrode-pair devices can be produced on separate substrates. The device can incorporate sensing electrodes in the same environment, which allows the electrodes to be coplanar and, thus, keep manufacturing costs low. Embodiments of the device can provide improvements to sensitivity, selectivity, and signal interference via surface temperature control.

Embodiments of the subject device can have a single pseudo-reference. Other embodiments can use all of the electrodes as pseudo-references with respect to each other. The electrodes can be viewed as making up "electrode-pairs," which can be measured as a potential difference signal. The voltage difference between two electrodes (which make up an "electrode-pair") is measured as the potential at one or each electrode changes. Embodiments can also have as a reference another fixed voltage, such as that provided by a battery, other power source or the chassis of an automobile.

Sensing electrodes can be metals (e.g., Platinum or Gold), semiconductors (e.g. semiconducting oxides such as $La_2CuO_4$ or $WO_3$), or any other material showing sensitivity to a single or multiple gas species. Typically, a given sensing electrode material will have varying sensitivity (i.e., changes in EMF) and selectivity to one or many different gas species. This depends on the temperature of each electrode and the difference in temperature between electrodes making up an electrode-pair. This will also depend on the concentration and chemical properties of the particular species interacting with the material. The degree of sensitivity and/or selectivity that changes depends on the material and its properties, gas species present, and the temperature. Since each electrode may be part of one or more "electrode-pairs," the number of measurable signals can be larger than the actual number of sensing electrodes.

The presence of more signals than actual number of electrodes can be an advantage in a device. Typically, with a greater number of signals the pattern recognition of multiple gas species becomes easier. The voltage response of electrode-pairs can be measured over a variety of known conditions, including exposures to one or more gas species concentrations, and these measurements can be used to interpret the measurements taken during exposures to unknown gas species concentrations (i.e., the sensor may be calibrated). Therefore, the result of having more signals than total number of electrodes means that a device will require fewer electrodes for the same or better selectivity. This, in turn, means reduced costs and the possibility of smaller devices.

The design of the sensor array can include, either as individual devices or together in a single device, two different "electrode-pair" schemes. One scheme uses multiple materials at the same time, which may be kept at the same and/or different temperature (using heating or cooling methods). A device may also include multiple electrodes of the same material that are maintained at one or more different temperatures.

The electrodes of the same material may be kept at the same temperature if other features of the electrode, such as microstructure (e.g., grain size or surface roughness), size, shape, or thickness, are different. Again, the gas sensor array may utilize one of these schemes or both of these schemes in a single device (or multiple devices), depending on the application.

Any given sensing electrode material is typically sensitive to more than one gas species. This sensitivity varies with temperature and gas species. Therefore, one can measure a signal from two electrodes of the same material if they are modified in a way that alters the sensitivity of at least one of the electrodes making up an electrode-pair. The sensitivity of a given electrode material can be modified by differences in its microstructure, geometry, temperature, or other method which changes the local environment of the electrode to enhance or alter chemical (or electrochemical) reactions in a desired way. The same modifications may be used to yield a measurable electrode-pair made up of dissimilar materials.

To be cost effective, the device(s) can be made on a single substrate. Furthermore, the device(s) can have sensing electrodes in the same environment, which allows the electrodes to be coplanar (i.e., all on one side of the substrate) and, thus, avoiding complex designs which might increase manufacturing costs. The sensitivity and selectivity of these sensors varies with temperature. Therefore, the temperature of such device(s) can be controlled and enabled to be modified quickly if the ambient temperature changes or if the electrode temperature changes for any other reason.

In order to achieve a device that is able to monitor two or more gas species of interest, an array of sensing electrodes can be used. The array signals can then be entered into algorithms to determine the concentrations of individual species. Pattern recognition can be implemented to determine the concentrations of individual species. By improving selectivity, a device can have fewer sensing electrodes to effectively detect the same species as a device with more signals but increased cross-sensitivities. This can simplify the device and lower the power consumption and the cost of constructing the device.

Heaters can be utilized with the subject invention in order to control the temperature of one or more of the sensing electrodes. Such heaters can use one or more heating elements through which current can be driven to create heat so as to alter the temperature of the sensing electrodes. The heating elements can use any conducting or resistive material (e.g., Platinum) which has the thermal and chemical stability necessary to keep it (and its performance) from degrading with time and in a harsh environment. The heating elements can act as resistors. The heat is produced via Joule heating, or passing electrical current through the heating elements. The heat generated is proportional to the square of the current multiplied by time. Additional embodiments can use a cooling apparatus to lower the temperature of the sensing electrodes. A variety of cooling techniques known to those skilled in the art can be incorporated into embodiments of the invention for this purpose.

Temperature control of embodiments of the subject devices can be accomplished in a number of ways. Precise control of temperature with minimal fluctuations is useful to achieving stable sensor signals. Therefore, thermal modeling can provide a way to design the temperature profile for the device. This information can be used when determining where to locate individual electrodes on the substrate of the array or how the temperature profile will change in varying gas flow velocities.

Surface temperature measurements can be difficult. Knowledge of the temperature of the sensing electrodes can enhance the device performance. The resistance of some metals, semiconductors, or other materials will change with temperature in a way which can be predicted by various mathematical models. After the data is fit to a model, software can easily calculate the surface temperature during sensor operation using the coefficients from the model and resistance measurements of the temperature sensor elements. In a specific embodiment, resistance measurements, or other temperature determining technique, can be applied to the sensing electrode, for example before or after the gas sensing measurement, in order to provide a value for the temperature of the sensing electrode. Additionally, temperature sensors that utilize changes in voltage (e.g., thermocouple) or capacitance as a detection method may also be integrated into the device.

Heating elements can be used not only to heat another object but also simultaneously as a temperature sensor. If the resistance of the heater can accurately be determined (e.g., using a four-wire method), then the temperature of the heating element (and thus that of the sensing electrode) can be calculated. Resistance typically increases as current is supplied to the heater because of Joule heating. This does not greatly affect the voltage or current measurements. That is to say, the measurements represent the actual current in the circuit and voltage drop across the heater. Therefore the calculated resistance, and hence temperature, of the heater represents the real value.

The heating element shape can be designed to ensure that temperature of any given sensing electrode is uniform, or, if desired, designed so that the temperature is purposefully non-uniform. The heating elements may be C-, spiral-, serpentine-shaped, or any other useful pattern to achieve the desired thermal distribution throughout the device. The heating elements can be controlled either by an applied voltage or current. The method that is chosen depends on the application. For example in an automobile, the likely power source will be the automobile's battery. The heating elements could, therefore, be voltage controlled.

A single heating element (or temperature sensor, or cooling element) or multiple heating elements (or temperature sensors, or cooling elements) may be used to control the temperature of any given sensing electrode(s).

Heating elements (or temperature sensors, or cooling elements) may be underneath (and appropriately aligned with) an individual or multiple sensing electrode(s), separated from the sensing electrode(s) and solid electrolyte by one or more thermally insulating or thermally conducting layers.

The heating elements (or temperature sensors, or cooling elements) may be separated from each other by thermally insulating or thermally conducting layers, by the geometry of the substrate or other layers, or by empty spaces between them.

The heating elements (or temperature sensors, or cooling elements) may be suspended in cavities for thermal isolation from other regions of the device.

The heating elements (or temperature sensors, or cooling elements) may also be completely covered by thermally insulating or thermally conducting layers (i.e., embedded in the device) and may exist in any of the device layers.

Platinum may be selected for the fabrication of heating elements, temperature sensors, and/or cooling elements. Platinum is an industry standard for high-temperature resistance-temperature-devices (RTD) and as heating elements in gas sensors because of durability and chemical and thermal stability. However, other materials may be used as heaters in such devices. Also, other materials may be used for the temperature sensors or cooling elements.

Also, with the incorporation of temperature control into such devices it may be possible to reverse electrode "poisoning" or other phenomena that keep the device from responding in a repeatable way for exposure to a given gas(es) and concentration(s) which results in changes in sensor performance over time or complete failure of the device.

Embodiments of the invention can improve selectivity of more than one gas species and/or can improve the sensitivity to more than one gas species. A single device with an array of electrode-pairs can both improve sensitivity and selectivity.

The device shown in FIGS. 1 and 2 includes a sensor array with integrated Platinum heater and temperature sensors that were fabricated for small size and low power-consumption. The array includes two (semiconducting) $La_2CuO_4$ (LCO) electrodes 1, 3 and a Platinum (Pt) reference electrode 2 all on the same side of rectangular, tape-cast Yttria-Stabilized-Zirconia (YSZ) substrate 4. In alternative embodiments, all three electrodes can be one material, such as LCO, or each electrode can be a different material. Platinum resistor elements are used as heaters 5 and/or temperature sensors 5, 6, 7 to control and monitor the temperature of the sensing electrodes. Finite Element Modeling was used to predict temperature profiles within the array. The array was then designed to keep LCO electrode 1 hotter with respect to the other two electrodes. The results from this device demonstrated that a gas sensor array with sensing electrodes kept at different temperatures can yield a device capable of selectively determining NO and $NO_2$ concentrations. The individual concentrations of these gases can be calculated during operation. Different sensing electrode materials and/or different temperature differentials between sensing electrodes can be used for detection of other gases and/or determination of the concentrations of other gases.

Referring to FIGS. 7-8, a different gas sensor array based on YSZ 12 includes two LCO sensing electrodes and two Platinum reference electrodes. The inner LCO 9 and Pt 10 electrodes are heated, while the outer LCO 11 and Pt 8 electrodes remain near the ambient temperature. Pt elements 14 and 15 are used to heat and measure temperature, while 13 and 16 are used only to measure temperature. This device offers the ability to measure the potential difference between multiple pairs of electrodes. In further embodiments, the heating elements and/or temperature sensing elements can be located on the same side of the substrate as the sensing electrodes or detached from the substrate.

From the trends with changes in specific electrode temperatures, the slopes of the plots in FIGS. 9-10 (and similar sensor response plots for the other electrode-pairs), which represent the sensitivity (mV change in signal per decade change in gas concentration) were used to make sensitivity plots in FIGS. 11-16. Each line represents a different heater setpoint, which in turn represents a separate temperature difference (|dT|) between the electrodes as shown. This was repeated for each of the six signals from the four sensing electrodes. In the trend plots, the case where |dT| is zero represents measurements when the heaters were not being operated.

FIG. 17A shows a contour plot for temperature variation in the sensor array of FIGS. 7-8 during operation. Each contour in the plot represents a given temperature within the device. A temperature profile through the middle of the device can be seen in FIG. 17B. Note that the sensor array of FIGS. 7-8 was made by hand and the results are therefore not necessarily ideal. Therefore, each of the electrodes, even when made of the same material, was slightly different from each other. When the electrode-pair is of the same material and the heater is not being operated, the sensitivity should be zero. However, as indicated in the plots the sensitivity is in fact nonzero.

Also note that the plots of FIGS. 9-16 are labeled to show the respective electrode-pairs, which make up six unique signals. In the plots, electrodes 8, 9, 10, and 11 from FIGS. 7-8 are designated as Pt(1), LCO(2), Pt(3), and LCO(4), respectively. At a certain setpoint, the unheated electrodes slightly began to increase in temperature due to the specific design of this array. This can be corrected very easily with minor changes in the design such as moving the unheated electrodes further away from the heated electrodes, or creating a thermal insulation barrier. The device can be improved with changes in the heater design and layout of the electrodes with respect to the heaters and to each other. Also, the heaters can be arranged differently with respect to each other. Thermal modeling helps determine what to expect in device performance with respect to temperature uniformity.

Referring to FIGS. 11 and 12, showing the signals from the LCO(4)-LCO(2) and Pt(3)-Pt(1) electrode-pairs, the sensitivity of the electrode pairs is changed as the temperature difference between them increases. For LCO(4)-LCO(2), the NO sensitivity significantly increases as the temperature of the heated electrode, LCO(2), rises. In fact there is almost an increase of ten times the initial sensitivity when no temperature difference exists between the electrodes. As the heater setpoints increase, the $NO_2$ sensitivity decreases to almost zero. There is a slight increase in sensitivity at later setpoints, but at least over a small range of the setpoints this electrode-pair is insensitive to $NO_2$. Therefore this electrode-pair shows sensitivity only to NO and should be NO selective. The signals from Pt(3)-Pt(1), further demonstrate that by changing the temperature of individual electrodes of the same material, the sensitivity can be changed.

Referring to FIGS. 13 and 14, showing the signals from the LCO(2)-Pt(3) and LCO(4)-Pt(1) electrode-pairs, the sensitivity of the electrode pairs is changed as the temperature difference between them increases. For LCO(2)-Pt(3), the electrode-pair effectively has become insensitive to NO. However, the $NO_2$ sensitivity becomes more positive and changes from a negative response to a positive response as the temperature difference between the electrodes increases. Therefore, this electrode-pair is selective to $NO_2$. For LCO (4)-Pt(1), the NO sensitivity remains nearly fixed at the level where the signal is without the heater in operation. This demonstrates that by changing the temperature of individual electrodes, the sensitivity can be changed for electrodes of different materials.

Referring to FIGS. 15 and 16, showing the signals from the LCO(4)-Pt(3) and LCO(2)-Pt(1) electrode-pairs, the sensitivity of the electrode pairs is changed as the temperature difference between them increases. For LCO(4)-Pt(3) the sensitivity to NO nearly doubles with respect to the condition without a difference in temperature between the electrodes.

Also, the sensitivity to $NO_2$ becomes more positive and changes from a negative response to a positive response as the temperature difference between the electrodes increases. This indicates that at some temperature difference between the two electrodes, the $NO_2$ sensitivity should go to zero. For LCO (2)-Pt(1), the NO sensitivity becomes increasingly negative as the temperature difference between the electrodes is increased. This shows that large changes in sensitivity to both NO and $NO_2$ are possible by having different temperatures of electrodes making up an electrode-pair.

FIGS. 18 through 21 demonstrate a variety of additional sensor embodiments that are possible. FIG. 18A represents a cross-section of a device similar to that shown in FIGS. 1 and 2 and FIGS. 7 and 8. In this embodiment, electrolyte layer 17 is still coupled with sensing electrodes 18 (which can be the same or different from each other). However, Pt elements 19 (used as heaters and/or temperature sensors), exist on top of support material 20. The support may be an electric insulator or electrolyte, which may be the same or different from electrolyte layer 17. The electrolyte 17 (and attached sensing electrodes 18) cover the Pt elements 19 and also sit atop the support 20. The embodiment shown in FIG. 18B is similar to that shown in FIG. 18A, with sensing electrodes 21 still being coupled to an electrolyte layer 22 on top of support 23. The main difference is that the Pt elements 24 are now embedded in the support 23. In FIG. 18C, the device incorporates a support material 25 with sensing electrodes 26 and electrolyte 27 on top. The electrolyte layer 27 is in contact with support 25. Pt elements 28 exist on the backside of support 25. FIG. 18D incorporates one electrolyte layer 29 for one (or more than one) electrode-pair made up of (same or different) sensing electrodes 30. Another electrolyte layer 31, also with sensing electrodes 30, exists separately from electrolyte 29. Both electrolyte layers 29 and 31 exist on top of support 32. Backside Pt elements 33 exist on the support as well. Multiple combinations of this arrangement are possible.

FIG. 19 shows a cross-section of an embodiment which has (same or different) sensing electrodes 34 on one side of an electrolyte 35, which has Pt elements 36 embedded in side. On the other side of electrolyte 36, are additional (same or different) sensing electrodes 37. Electrode pairs may be made up of any combination of sensing electrodes 34 and 37. Having sensing electrodes on opposite sides of the device results in a separation of the local gaseous environment around each sensing electrode, and in certain situations will result in a reduction of cross-talk and improved selectivity.

FIG. 20 is a cross-section of an embodiment which has a hollow chamber in the middle of the device. In a fashion similar to that used in the embodiment of FIG. 19, this chamber acts to separate the local environment of the sensing electrodes and can be used to provide a separate gas stream of known concentration as a reference. The device incorporates (same or different) sensing electrodes 38 on the outside and (same or different) sensing electrodes 39 inside of the hollow space and attached to electrolyte 40. Pt elements 41 may exist on the inside (or outside) of the chamber, also attached to electrolyte 40. Additional Pt elements for heating or temperature sensing may be arranged about the device in various locations.

FIGS. 21A and 21B show the top view of embodiments where the electrode arrangement relative to the substrate is different from that shown in FIGS. 1 and 2 and FIGS. 7 and 8. FIG. 21A shows an embodiment with (same or different) sensing electrodes 42 atop an electrolyte and/or structural support 43. Compared to other embodiments, the sensing electrodes 42 are staggered and separated from each other on the top of the electrolyte (support) 43. FIG. 21B shows an embodiment where the sensing electrodes 44 are oriented in a different manner with respect to the electrolyte and/or support 45 and gas flow direction than the embodiment shown in FIG. 21A. Various arrangements and features such as those shown in other embodiments may be used for Pt elements (used as heaters and/or temperatures sensors), other temperature sensors or cooling elements, with respect to these and other embodiments.

FIGS. 22 through 31 represent signals from the device in FIGS. 7 and 8, demonstrating that using a method and/or apparatus in accordance with embodiments of the invention, a sensor array can be made selective to a specific gas species as the temperature of individual electrodes is changed. Again, the difference in the temperature between electrodes and the absolute temperature of each electrode is important for sensor performance. FIGS. 22 through 25 show the $NO_x$ gas mixture results for the LCO(2)-Pt(1) signal, while the LCO(4)-LCO (2) signal is demonstrated in FIGS. 26 through 31.

FIG. 22 represents the LCO(2)-Pt(1) sensor response to $NO_2$ gas exposure for gas mixture conditions of 0 ppm NO (solid lines) and 200 ppm NO (dashed lines). The x-axis of the plot has a log scale. The square, circle, and diamond symbols represent the conditions where 0, ~13, and ~54 mW of total power were delivered to the Pt heating elements resulting in greater temperature differences (dT) between electrodes. As can be seen, the slope of each set of lines, which represents the sensitivity (mV change in signal per decade change in gas concentration) to $NO_2$, increases with application of heater power. Furthermore, the sensitivity is mostly unaltered by addition of NO during $NO_2$ exposure. FIG. 23 shows the sensor response for NO gas exposure with 0 ppm $NO_2$ (solid lines) and 200 ppm $NO_2$ (dashed lines). The x-axis of the plot has a log scale. As seen in FIG. 23, the sensitivity to NO decreases as the power to the heaters increases. Also marked in this figure for each heater setpoint are the approximate shifts in NO sensitivity when 200 ppm $NO_2$ is added to the gas mixture. The shifts are all negative as expected when considering the larger (negative) response to $NO_2$ as shown in FIG. 22. As the heater power increases, the shift becomes more uniform over the entire range of NO concentrations probed. At lower heater power, the shift is more prominent for higher NO concentrations (i.e., the sensitivity decreases with addition of 200 ppm $NO_2$). Without the use of the heaters, the shift in the sensor response is 0.18 to 1.3 mV along the entire NO concentration range. For 13 mW of heater power, the shift is between 3.2 and 3.7 mW. At 54 mW, the heater power is sufficient to reduce the NO response to such a degree that the curve is horizontal. When 200 ppm $NO_2$ is introduced, the curve remains horizontal but shifts to more negative values by 6.8 mV.

FIG. 24 shows the $NO_2$ sensor response with the same conditions as FIG. 22 for 0 ppm NO. However, the x-axis has a linear scale and this plot includes data points for the condition of 0 ppm $NO_2$. Also marked in FIG. 24, are the difference in the measured voltage difference between the 0 ppm $NO_2$ baseline and the 200 ppm $NO_2$ gas step. When the results for NO (0 ppm and 200 ppm $NO_2$) in FIG. 23 are compared to the changes in voltage between the 0 ppm $NO_2$ baseline and 200 ppm $NO_2$ gas step (FIG. 24), the improvements in $NO_2$ selectivity with increasing heater power are clear. Without the use of the heaters, a change from 0 ppm to 200 ppm $NO_2$ produces a change in voltage of 3.5 mV (FIG. 24), while there is a shift of 0.18 to 1.3 mV between these two conditions when NO is also present in the gas mixture (FIG. 23). This difference can be debilitating when trying to determine NO and/or $NO_2$ gas concentrations in a gas mixture because the actual voltage measured is different from that which is expected. When a small amount of power is delivered to the heaters (~13 mW), the situation improves slightly as evidenced when comparing the expected change in voltage of 5 mV (FIG. 24) to the actual change of 3.2 to 3.7 mV seen when NO and $NO_2$ are present (FIG. 23). As mentioned previously, a heater setpoint delivering 54 mW of power results in increased $NO_2$ sensitivity (FIG. 22) and a complete removal of NO sensitivity (horizontal curve in FIG. 23). Furthermore, the expected voltage change between conditions of 0 ppm and 200 ppm $NO_2$ is 6.5 mV (FIG. 24). This is almost exactly the same as the shift (6.8 mV) during NO gas exposure when measurements are also made in the presence of 0 ppm and 200 ppm $NO_2$. Now that gas mixtures of NO and $NO_2$ do not affect the expected voltage change to variations in $NO_2$, the gas sensor array can be used to accurately portray the real concentration of $NO_2$ gas present in the gas mixture. Using the same principles, the sensor array can be made to have improved selectivity to any gas, such as NO, $NO_2$, $NH_3$, CO, $CO_2$, and/or hydrocarbons.

FIG. 25 shows a plot of sensitivity versus total heater power for the LCO(2)-Pt(1) signal of the embodiment in FIGS. 7 and 8 with gas mixture conditions of NO (0 and 200 ppm $NO_2$) and $NO_2$ (0 and 200 ppm NO), as indicated. The sensitivity to NO, with and without the presence of $NO_2$, decreases to 0 mV/decade ppm NO as the heater power increases. As this happens, there is also a decrease in the change in sensitivity seen when 200 ppm $NO_2$ is introduced into the gas mixture. The sensitivity to NO, with and without the presence of $NO_2$, decreases to 0 mV/decade ppm NO as the heater power increases. As the heater power increases, the sensitivity to $NO_2$, with and without the presence of NO, almost increases by a factor of 2. The sensitivity to $NO_2$ with 0 ppm and 200 ppm NO, remains mostly unchanged over the same range of heater power. Moreover, by operating this electrode pair at the maximum dT (obtained with 54 mW of heater power) a sensor is obtained that has both higher sensitivity and selectivity to $NO_2$, since the cross sensitivity to NO is removed (becomes zero or negative). When considering these changes in sensitivity and the voltage shifts observed with exposure of gas mixtures of NO and $NO_2$ as mentioned earlier, it is clear that the overall sensor array performance can be enhanced using embodiments of the subject method.

FIGS. 26 through 28 show how the LCO(4)-LCO(2) electrode-pair, of the embodiment of FIGS. 7 and 8, can be used to detect total NO concentrations when NO and $NO_2$ exist in a gas mixture together. The LCO(4)-LCO(2) response to $NO_2$ gas exposure for gas mixture conditions of 0 ppm NO (solid lines) and 200 ppm NO (dashed lines) is shown in FIG. 26 for total heater power of 0, 13, and 54 mW as indicated. For the same total heater power, FIG. 27 shows the response to NO gas exposure for gas mixture conditions of 0 ppm $NO_2$ (solid lines) and 200 ppm $NO_2$ (dashed lines). Referring to FIGS. 26 and 27, the response to $NO_2$ (0 and 200 ppm NO) gas mixtures always shows a positive response. The same is true for NO (0 and 200 ppm $NO_2$) gas mixtures and except for the case when the heaters are not used (0 mW total heater power), where there is essentially no sensitivity to NO. Furthermore, the shift in the LCO(4)-LCO(2) signal is always positive when NO is introduced to $NO_2$ gas steps, as in FIG. 26, and when $NO_2$ is added to NO gas steps, as in FIG. 27. When there is a shift in response for both the case in FIGS. 26 and 27, the slope remains relatively unchanged, even at the higher total heater power setting. This is shown in FIG. 28, which is a plot of sensitivity (mV/decade ppm NO or $NO_2$) versus total heater power for NO (0 and 200 ppm $NO_2$) and $NO_2$ (0 and 200 ppm NO), as indicated. Also note in this figure, that the sensitivity to both NO and $NO_2$ increases with increasing total heater power as the temperature of the LCO(2) electrode increases. A unique voltage difference is produced for each combination of NO and $NO_2$ concentrations. This is demonstrated in FIGS. 29 through 31, which show the sensor response versus total ppm NO in the gas mixture for 0 mW, 13 mW, and 54 mW respectively. In the case where the heaters are not used (FIG. 29), the LCO(4)-LCO(2) signal is insensitive to NO but has sensitivity to $NO_2$. Therefore, under these conditions the LCO(4)-LCO(2) electrode-pair is selective to $NO_2$. However, as evident from FIGS. 29 through 31, as the temperature of the heated LCO(2) electrode increases (i.e., when the heater power is applied), the total $NO_x$ measurement becomes possible as the signal begins to become sensitive to NO, while remaining sensitive to $NO_2$. Comparing FIGS. 30 and 31, as the heater power is increased further, the sensitivity to NO and $NO_2$ increases even more. Furthermore, there is overlap between the gas mixture measurements involving NO (0 and 200 ppm $NO_2$) and $NO_2$ (0 and 200 ppm NO). For example, at a total NO concentration of 400 ppm (200 ppm NO and 200 ppm $NO_2$), the sensor response is exactly the same regardless of whether the measurement was made in dynamic gas steps of $NO_2$ with static NO concentration, or vice versa. In summary, by changing the temperature of at least one sensing electrode with respect to another, it becomes possible to measure the total NO in gas mixtures of NO and $NO_2$ even when using the same materials for each electrode making up the electrode-pair.

As demonstrated in FIGS. 22 through 31, the embodiment in FIGS. 7 and 8 and similar sensor arrays have the capability of detecting the individual concentrations of NO and $NO_2$. This is possible because the LCO(2)-Pt(1) electrode-pair can selectively detect $NO_2$ over NO in NO gas mixtures when the LCO(2) electrode is heated locally. Furthermore, the LCO(4)-LCO(2) electrode-pair, which is made up of two sensing electrodes of the same material but different temperatures, is able to detect total $NO_x$. The concentration of NO can be calculated by subtracting the detected $NO_2$ concentration from the detected $NO_x$ concentration. Though this method is indirect, it is possible that using the same method of locally heating individual electrodes making up electrode-pairs of similar or different temperatures that an electrode-pair(s) can provide selective detection of NO, $NO_2$, (or CO, $CO_2$, ammonia, and other gases) as demonstrated in FIGS. 9 through 16.

DETAILED DISCLOSURE

Figure 1:
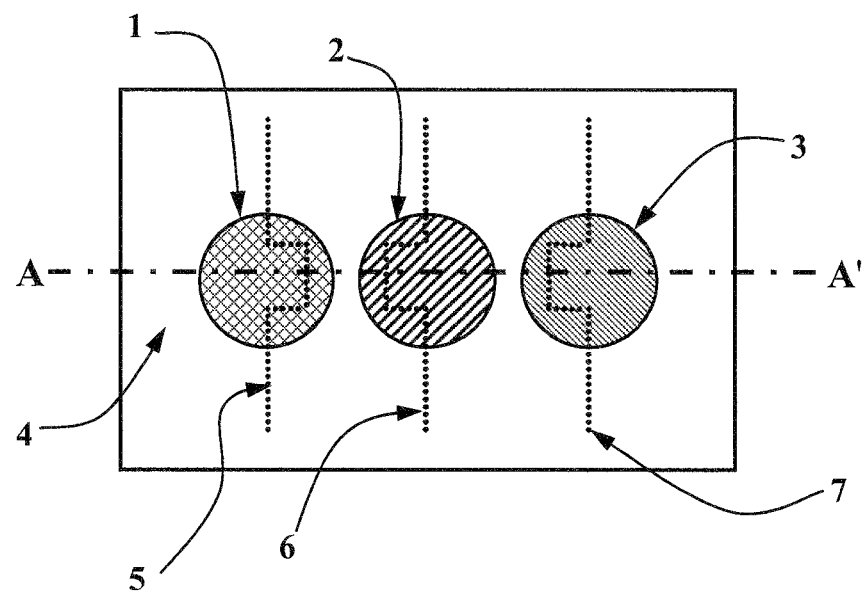
FIG. 1 shows a specific embodiment of a device in accordance with the subject invention.

Embodiments of the subject invention relate to a gas sensor and method for sensing on or more gases specific embodiments pertain to a potentiometric gas sensor and method for sensing on or more gases. Additional embodiments are directed to amperometric and/or impedimetric gas sensors and method for sensing one or more gases. An embodiment incorporates an array of sensing electrodes maintained at similar or different temperatures, such that the sensitivity and species selectivity of the device can be fine tuned between different pairs of sensing electrodes. A specific embodiment pertains to a gas sensor array for monitoring combustion exhausts and/or reaction byproducts. An embodiment of the subject device related to this invention operates at high temperatures and can withstand harsh chemical environments.

Embodiments of the device can have sensing electrodes in the same environment, which allows the electrodes to be coplanar. The sensitivity and selectivity of these sensors can vary with temperature. Therefore, with respect to specific embodiments, the temperature of the device can be precisely controlled and can be changed rapidly when desired. In order to achieve a device that is able to monitor two or more gas species of interest, an array of sensing electrodes can be incorporated. The array signals can then be entered into linear algorithms (or other appropriate algorithm(s)) to determine the presence of and/or concentrations of one or more individual species. As pattern recognition is not an easy task to accomplish and may require additional electronics, thereby driving up the cost of the device, it may be preferred to have the capability of individually monitoring a single species in the presence of others, with minimal interference. In this way, the device will not require extensive pattern recognition, if any at all.

Embodiments of the invention can provide improvements in selectivity and sensitivity via thermal modification of individual sensing electrodes and/or the entire device. Furthermore, improvements in signal noise can be achieved if the temperature is uniformly maintained. Also, with the incorporation of temperature control into embodiments of the subject device, it is possible to reduce or reverse electrode "poisoning" or other phenomena that results in changes in sensor performance over time or complete failure of the device.

The subject method and device can be used for the monitoring of combustion byproducts or other processes for chemical/gas monitoring. In a specific embodiment, the device can be used to monitor the exhausts in automobiles to determine if the catalytic converter has malfunctioned or to provide information for adjusting the air-to-fuel ratio in the engine based on EPA (or other) requirements, which will change as driving conditions differ. The subject device may also be used to monitor combustion byproducts (or other chemical/gas related processes) at a power plant or any industrial manufacturing processes.

An embodiment of a sensor array in accordance with the invention incorporates an integrated Platinum heater and temperature sensors fabricated for small size and low power-consumption. The array includes two $La_2CuO_4$ electrodes and a Platinum reference electrode all on the same side of a rectangular, tape-cast YSZ substrate. Platinum resistor elements are used as heaters and/or temperature sensors to control and monitor the temperature of the sensing electrodes. Finite Element Modeling was used to predict temperature profiles within the array. The array was then designed to keep one $La_2CuO_4$ electrode hot with respect to the other two electrodes. The results of from this device demonstrated that a gas sensor array with sensing electrodes kept at different temperatures can yield a device capable of selectively determining NO and $NO_2$ concentrations. In additional embodiments, the selectivity of a sensor array can be enhanced through control of the local temperature of the sensing electrodes.

Control of the local temperature of the sensing electrodes can be implemented by cooling in addition to or instead of heating. Passive and/or active cooling techniques known in the art can be incorporated with the subject invention.

Sensing electrodes can be made from metals (e.g., Platinum), semiconductors (e.g. semiconducting oxides such as $La_2CuO_4$ or $WO_3$), or other material showing sensitivity to a gas. In general, any given sensing electrode material will have varying sensitivity and selectivity to different gas species depending on the temperature of the electrode. The degree to which sensitivity and/or selectivity that changes depends on the material, gas, and temperature. Each electrode may be part of one or more "electrode-pairs". This means that the measurable number of signals can be larger than the actual number of sensing electrodes. Specifically, the design of the sensor array can include (either as individual devices or together in a single device) two different "electrode-pair" schemes. One scheme can use multiple materials at the same time, which may be kept at the same and/or different temperature. The control of the temperature can be accomplished via heating and/or cooling techniques. A device may also incorporate multiple electrodes of the same material that are maintained at one or more different temperatures. Electrodes of the same material may be kept at the same temperature, one or more other features of the electrodes, such as microstructure, size, or thickness, can be different for different electrodes. Accordingly, the gas sensor arrays may utilize one or more of these schemes in a single device, depending on the application.

Gas sensors in accordance with the invention can incorporate specifically designed heating elements to control the temperature topside of individual sensing electrodes. In an embodiment, the sensing electrodes are on topside of, and the heating elements are on the backside, of a substrate. In another embodiment, the sensing electrodes are on both sides of the substrate. The substrate can be, for example, a YSZ substrate or other electrolyte. The substrate may also be a structural support, such as $Al_2O_3$, with an electrolyte layer on top. The heating elements can be made of any material, such as platinum, that has the thermal and chemical stability to not degrade with time in a harsh environment. The heating elements can act as resistors and produce heat via Joule heating, by passing electrical current through the heating elements.

In accordance with various embodiments of the subject invention, a variety of electrolyte materials for the substrate can be used and a variety of materials can be used for the sensing electrode and any heating elements can be used. Examples of suitable materials are taught in U.S. Pat. No. 6,598,596, which is incorporated herein by reference in its entirety. The electrodes can be made from a variety of materials, including metals, and semiconductors. The semiconductor material is preferably a metal oxide or a metal oxide compound. The terms "metal oxide" and "metal oxide compound" are used interchangeably herein to mean a compound having elemental metal combined with $O_2$. Examples of metal oxides that are useful in the invention include $SnO_2$, $TiO_2$, TYPd5, $MoO_3$, $ZnMoO_4$ (ZM), $WO_3$, $La_2CuO_4$, and mixtures thereof. The semiconductor materials can include a metal oxide. The metal oxide is preferably $SnO_2$, $TiO_2$, TYPd5, $MoO_3$, or $ZnMoO_4$, where TYPd5 is an acronym defined below. The acronym TYPd5 is used herein to represent a composite prepared by selecting $TiO_2$ (titania), $Y_2O_3$ (yttria) and Pd in a weight ratio of approximately 85:10:5.

The electrolyte is preferably an oxygen ion-conducting electrolyte. The oxygen ion-conducting electrolyte can be based on $ZrO_2$, $Bi_2O_3$ or $CeO_2$. Preferred oxygen ion-conducting electrolyte are electrolyte mixtures, the mixtures generally including a base material, such as $ZrO_2$, $Bi_2O_3$ or $CeO_2$ and one or more dopants, such as calcia (CaO) and yttria ($Y_2O_3$) which can function as stabilizers, or some other suitable oxygen ion-permeable material. For example, yttria stabilized zirconia (YSZ) electrolytes can be formed by mixing yttria and $ZrO_2$. Electrolytes that conduct ionic species other than oxygen ions, e.g., halides, are well known in the art and also find utility in the invention for measuring halogen-containing gas species. The choice of material for electrolyte can depend on the component in the gas mixture to be measured. Thus, to measure the concentration of an oxide component, for example, $NO_x$, $CO_x$, or $SO_x$ the electrolyte is preferably an oxygen-ion conducting electrolyte. Preferred oxygen ion-conducting electrolytes are electrolyte mixtures based on zirconia ($ZrO_2$), bismuth oxide ($Bi_2O_3$), and ceria ($CeO_2$). Practical electrolyte mixtures generally include one or more dopants, such as calcia (CaO) and yttria ($Y_2O_3$), or some other suitable oxygen ion-permeable material.

A specific embodiment of a gas sensor array includes two LCO sensing electrodes and two Platinum reference electrodes. The inner LCO and Pt electrodes are heated, while the outer LCO and Pt electrodes remain near the ambient temperature. Furthermore, the potential difference between multiple pairs of electrodes can be measured in order to provide signals. Since no two electrodes have the same combination of material and operating temperature, there are a total of six distinct signals that can be measured by pairing the four electrodes. These signals can be compared to help determine the gas concentrations in a mixture of gases.

The temperature control of these devices can be important. Precise control of temperature with minimal fluctuations can allow the device to produce stable sensor signals. Therefore, thermal modeling can be performed during the design phase to provide information regarding the temperature profile in the device for different locations of the sensing electrodes and the heating electrodes on the substrate of the array.

Platinum can be used for the fabrication of heating elements and temperature sensors. Platinum is an industry standard for high-temperature resistance-temperature-devices (RTD) and as heating elements in gas sensors because of durability and chemical and thermal stability. However, other materials may be used as heaters in the subject devices.

Surface temperature measurements can be difficult and some of the best methods available include use of optical infrared sensors and RTDs. Below approximately 400° C. the resistance of Platinum has a linear dependence on temperature. However, above this temperature, further heat loss causes the linear model to deviate from experimental data, and an alternative model is $$R(T)=a(1+bT-cT^2) \quad (1)$$

where a, b, and c are empirical coefficients. After the data is fit to the model, software can calculate the surface temperature during sensor operation using the coefficients from (1) and resistance measurements of the Platinum elements.

Heating elements can be used not only to heat another object but also simultaneously as a temperature sensor. If the resistance of the heater can accurately be determined (e.g., using a four-wire method), then the temperature of the Platinum element can be calculated. Resistance increases as current is supplied to the heater because of Joule heating. This does not greatly affect the voltage or current measurements. That is to say, the measurements represent the actual current in the circuit and voltage drop across the heater. Therefore the calculated resistance, and hence temperature, of the heater represents the real value.

The heating element shape is important to the temperature distribution. In an embodiment, the temperature of the sensing electrode is uniform, or, if desired, nonuniform in a preferred manner. In an embodiment, the heating elements are C-shaped. Serpentine-patterned heaters can also be utilized. Spiral shaped heaters, or any other shaped heaters, can also be used. The heating elements can be controlled either by an applied voltage or current. The method of controlling the heating elements utilized depends on the application. As an example, in an automobile, the automobile's battery can be the power source, such that the heating elements would be voltage controlled.

In a specific embodiment, a YSZ substrate can have multiple sensing electrodes on one side. Platinum (or other resistive material) elements are on the opposite side of the YSZ substrate, aligned with the electrodes. The sensing electrodes may also be oriented in a symmetric or nonsymmetrical fashion with respect to each other, and they may be staggered. The Platinum (or other resistive material) elements need not be used as heaters. The Platinum elements may be used as heaters and/or temperature sensors. In another embodiment, the semiconductive elements can be used for cooling of the electrodes via, for example, thermoelectric cooling. The cooling elements may also be made of any material which allows cooling of specific regions in the device. The thermal characteristics of the heating/cooling elements and/or surface temperature sensors can be improved with the use of insulating materials integrated into the device structure or by other specific shape or design change to the device that impacts the thermal properties of the device, such as empty volumes. The shape of the substrate can also vary.

Figure 2:
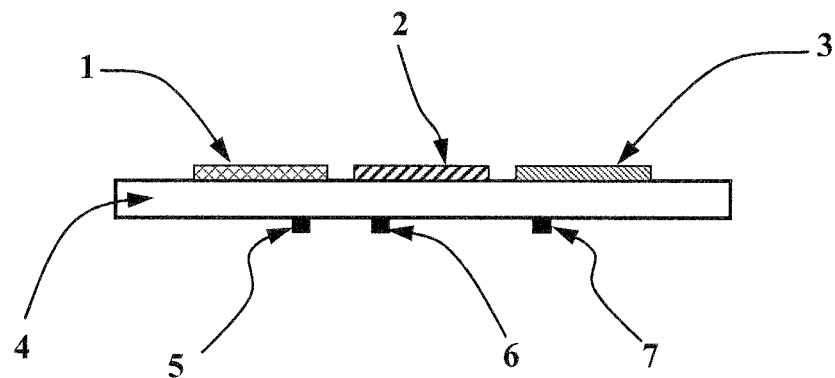
FIG. 2 shows a cross-sectional view of the embodiment of FIG. 1.
Figure 3:
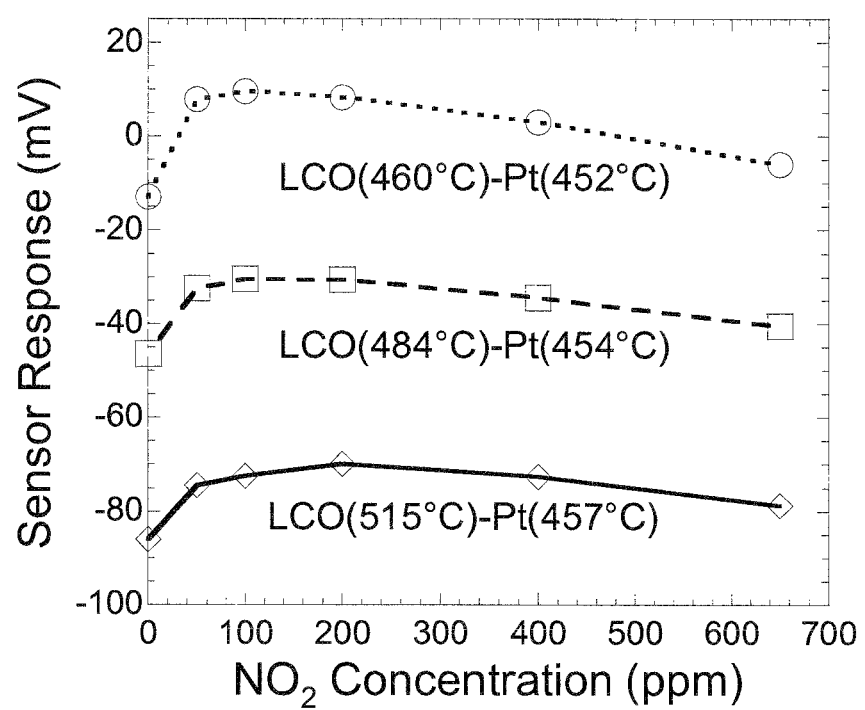
FIG. 3 shows the sensor response vs. concentrations of $NO_2$ for the non-heated LCO electrode vs. the non-heated platinum electrode taken from the three sensing electrodes.
Figure 4:
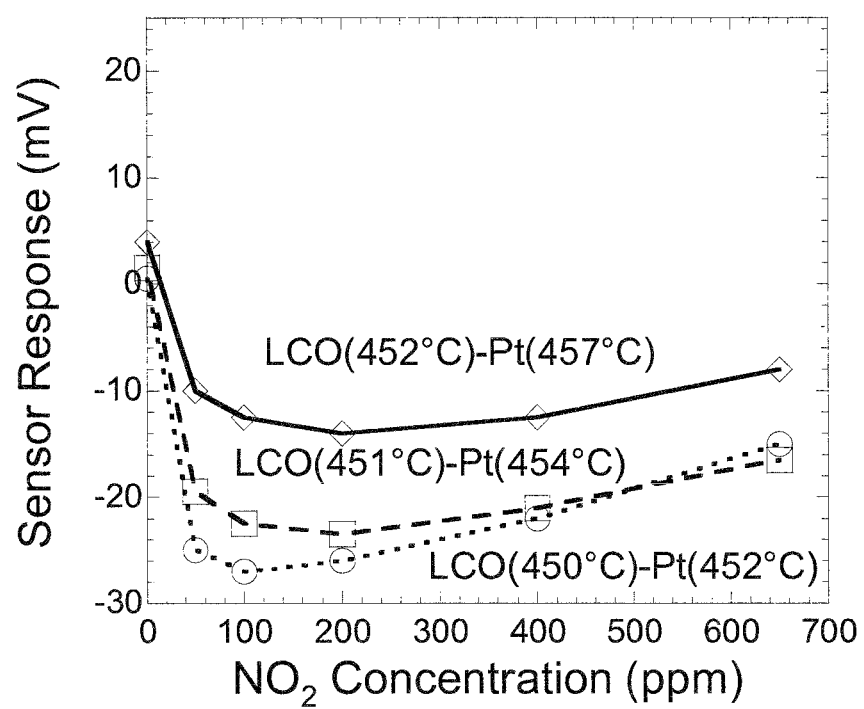
FIG. 4 shows the sensor response vs. concentrations of $NO_2$ for the heated LCO electrode vs. the non-heated platinum electrode taken from the three sensing electrodes.
Figure 5:
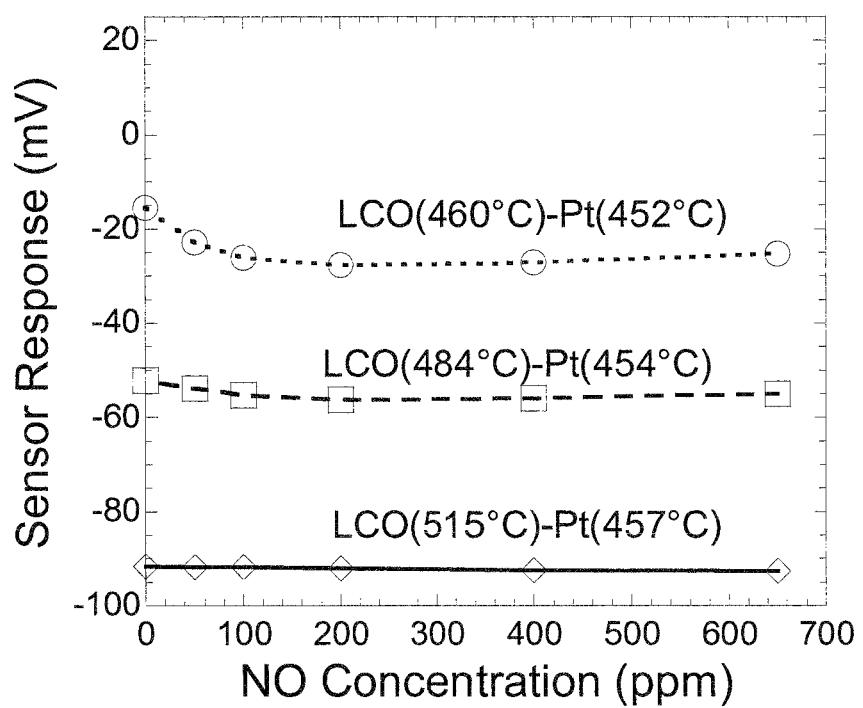
FIG. 5 shows the sensor response vs. concentrations of $NO_2$ for the heated LCO electrode vs. the non-heated platinum electrode taken from the three sensing electrodes.
Figure 6:
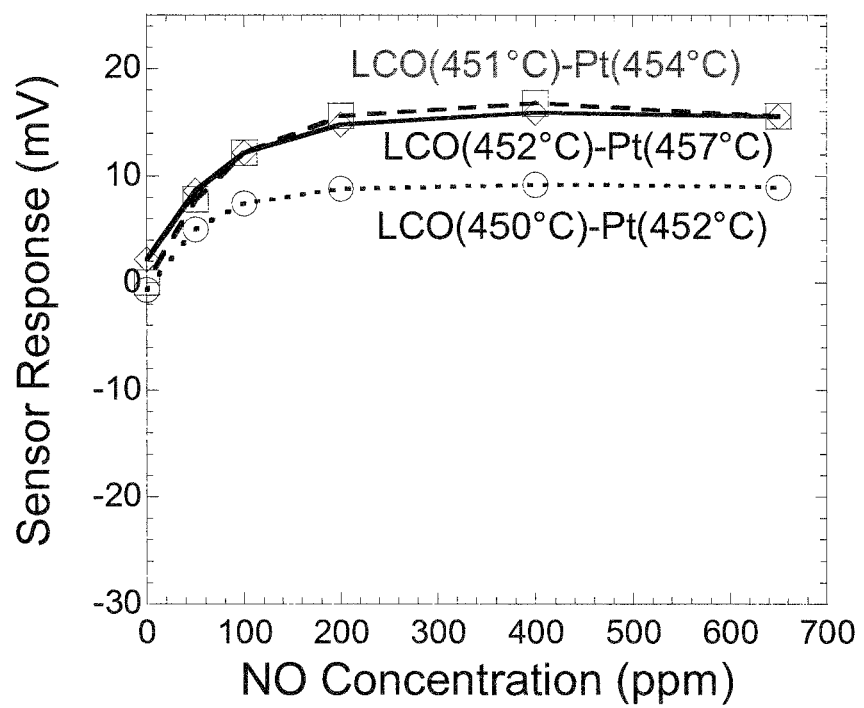
FIG. 6 shows the sensor response vs. concentrations of $NO_2$ for the non-heated LCO electrode vs. the non-heated platinum electrode taken from the three sensing electrodes.

FIG. 1 shows a specific embodiment of a device in accordance with the subject invention, and FIG. 2 shows a cross-sectional view of the same embodiment. The device includes two $La_2CuO_4$ electrodes with a Platinum electrode in between, on a first side of a substrate, where the substrate is an electrolyte. A Platinum heater and two Platinum temperature sensing elements can be positioned on the other side of the substrate. FIGS. 3-6 show the sensor response vs. concentrations of NO and $NO_2$ for two different electrode-pair combinations taken from the three sensing electrodes. These results show that the device was able to produce a signal that was mainly sensitive to $NO_2$ and a signal that was sensitive to both NO and $NO_2$. Thus, indirect detection of individual concentrations of NO and $NO_2$ is possible via substraction.

Figure 7:
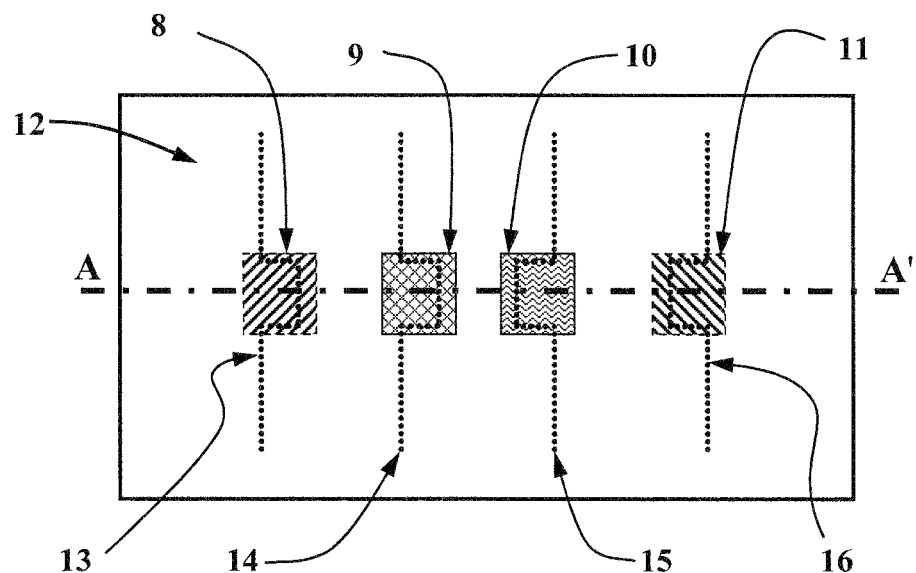
FIG. 7 shows an additional embodiment of the subject invention.
Figure 8:
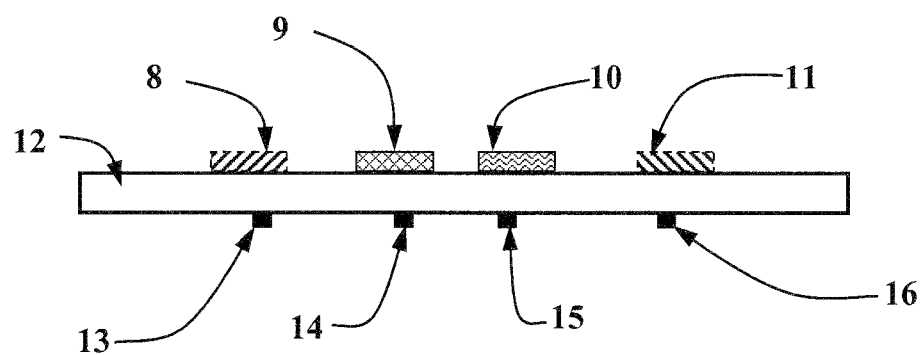
FIG. 8 shows a cross-sectional view of the embodiment in FIG. 7.
Figure 9:
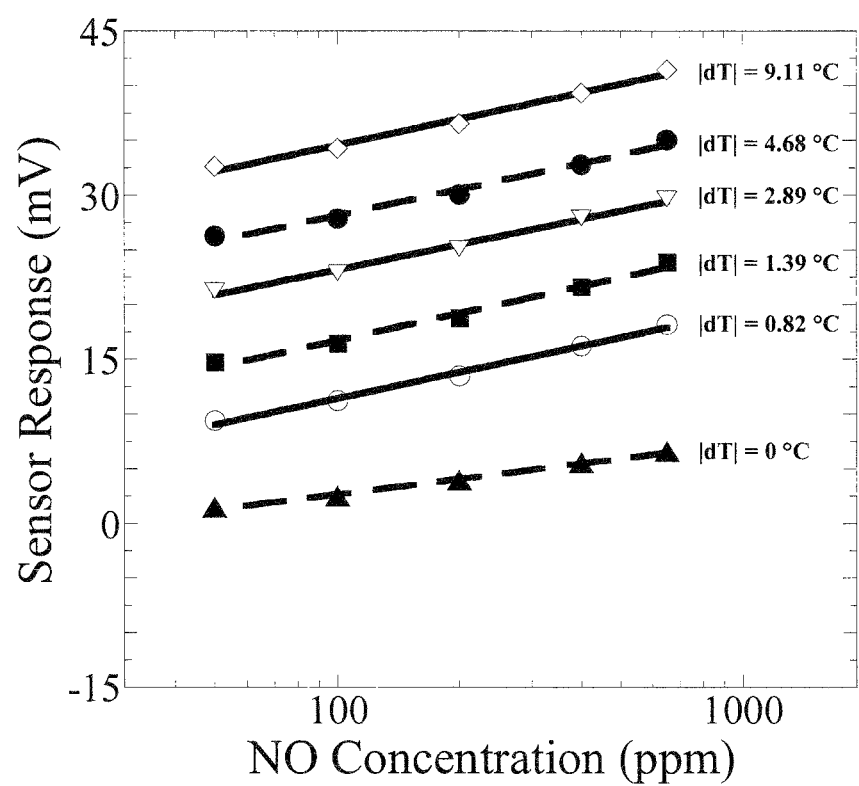
FIG. 9 shows the sensor response vs. concentrations of NO for the electrode pair having the non-heated LCO sensing electrode and the heated platinum sensing electrode, LCO(4)-Pt(3), showing the results for increasing temperatures difference.
Figure 10:
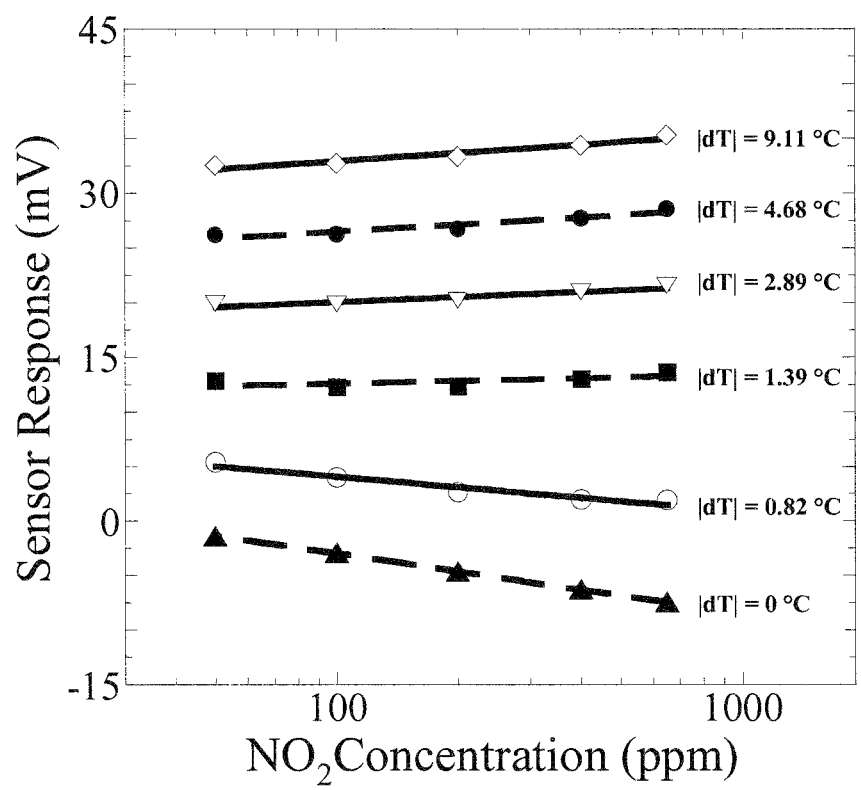
FIG. 10 shows the sensor response vs. concentrations of $NO_2$ for the electrode pair having the non-heated LCO sensing electrode and the heated platinum sensing electrode, LCO(4)-Pt(3), showing the results for increasing temperatures.
Figure 11:
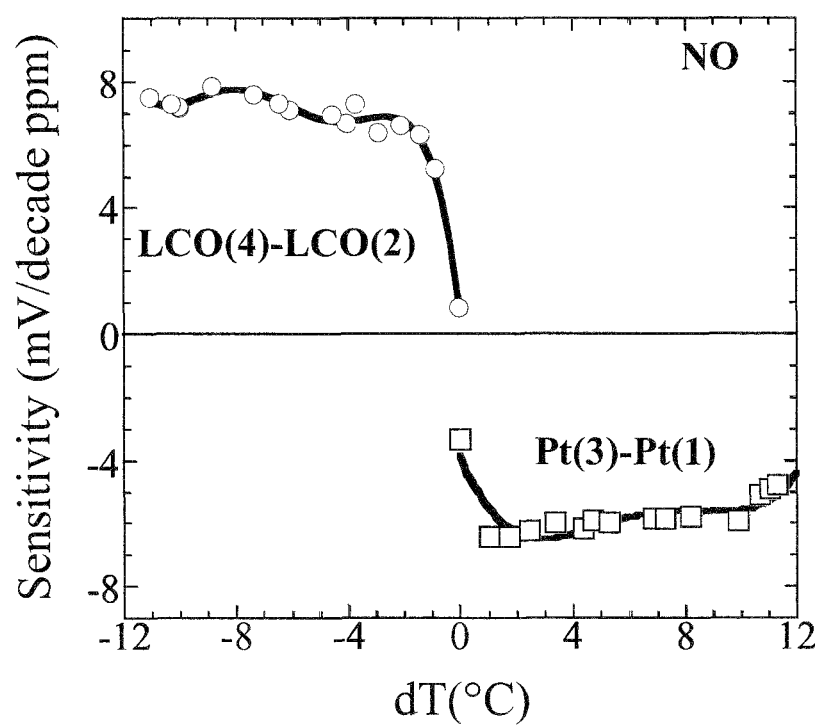
FIG. 11 shows the signal results from the LCO(4)-LCO(2) and Pt(3)-Pt(1) electrode-pairs, of the embodiment in FIGS. 7 and 8, in response to changes in gas concentration of NO.
Figure 12:
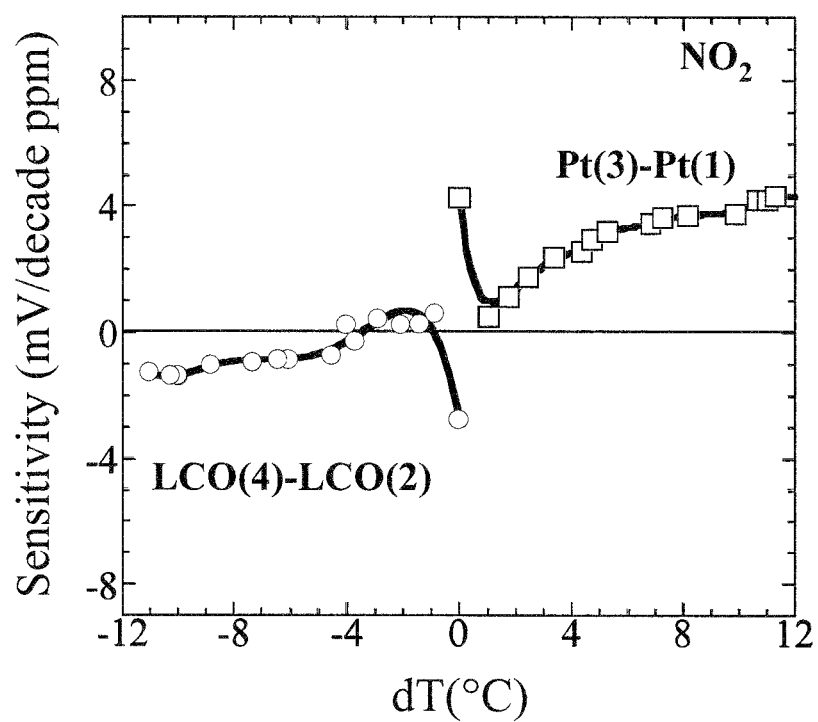
FIG. 12 shows the signal results from the LCO(4)-LCO(2) and Pt(3)-Pt(1) electrode-pairs, of the embodiment in FIGS. 7 and 8, in response to changes in gas concentration of $NO_2$.
Figure 13:
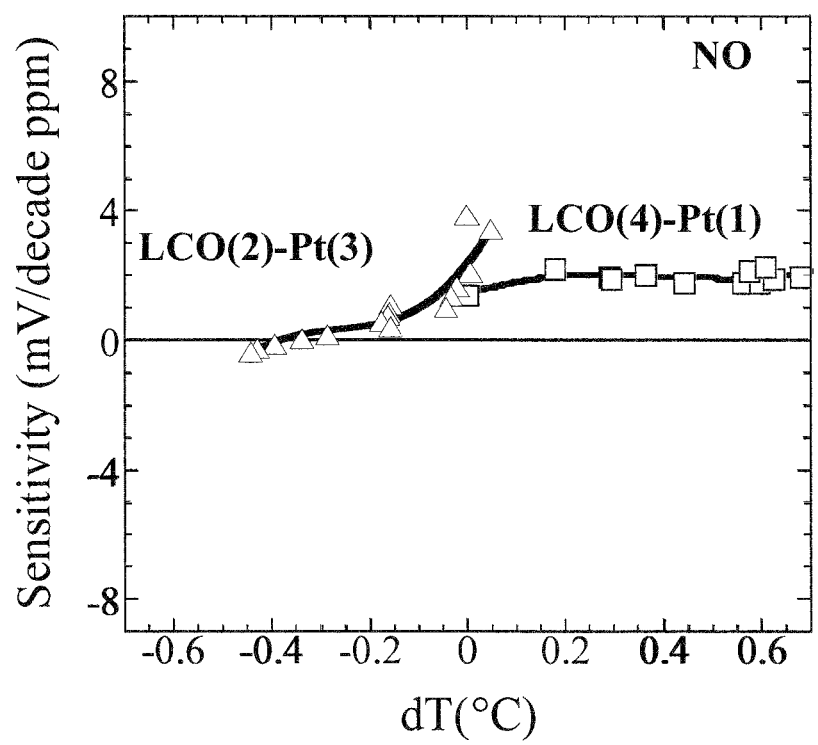
FIG. 13 shows the signal results from the LCO(2)-Pt(3) and LCO(4)-Pt(1) electrode-pairs, of the embodiment in FIGS. 7 and 8, in response to changes in gas concentration of NO.
Figure 14:
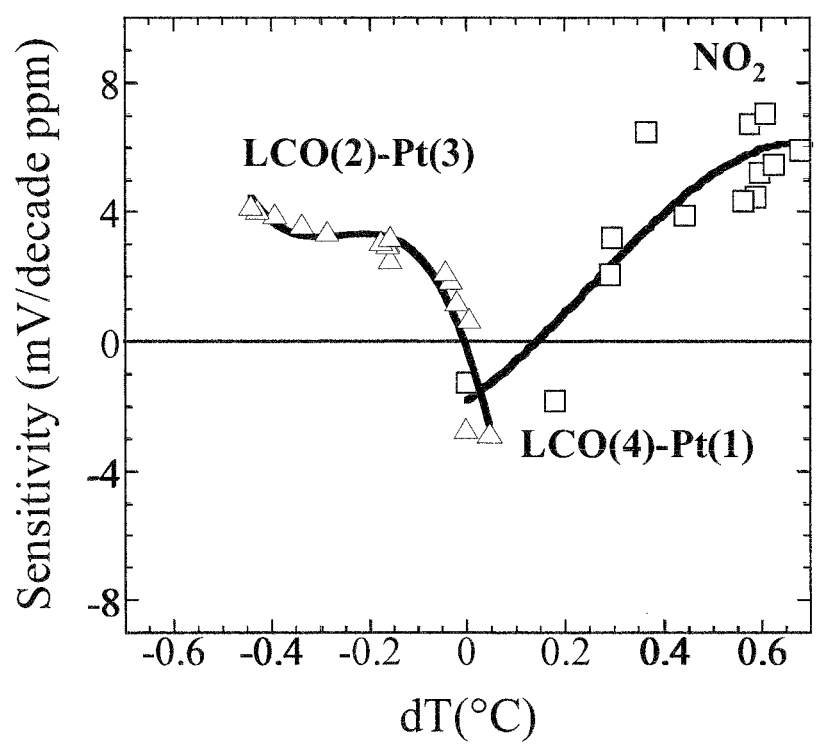
FIG. 14 shows the signal results from the LCO(2)-Pt(3) and LCO(4)-Pt(1) electrode-pairs, of the embodiment in FIGS. 7 and 8, in response to changes in gas concentration of $NO_2$.
Figure 15:
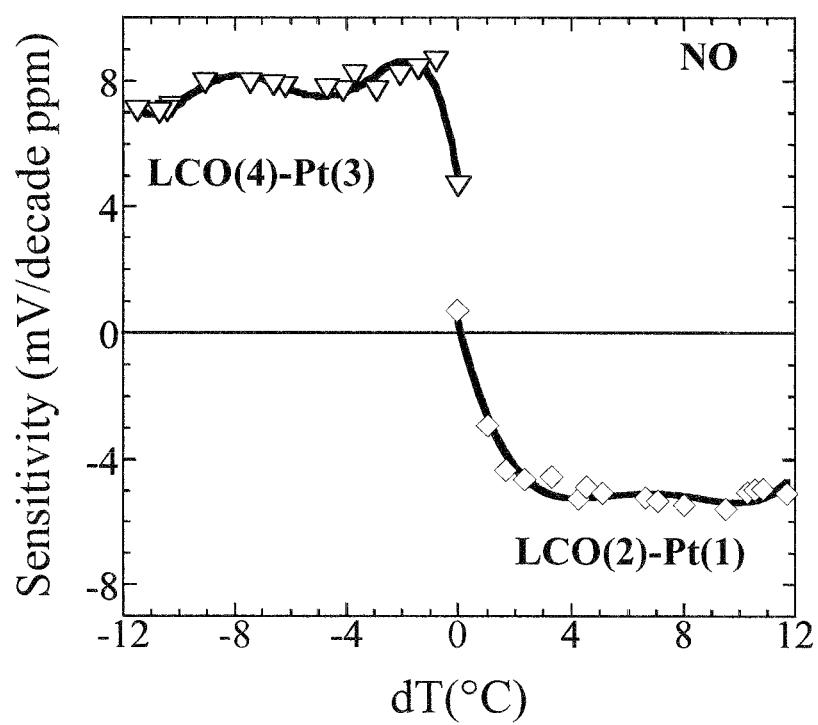
FIG. 15 shows the signal results from the LCO(4)-Pt(3) and LCO(2)-Pt(1) electrode-pairs, of the embodiment in FIGS. 7 and 8, in response to changes in gas concentration of NO.
Figure 16:
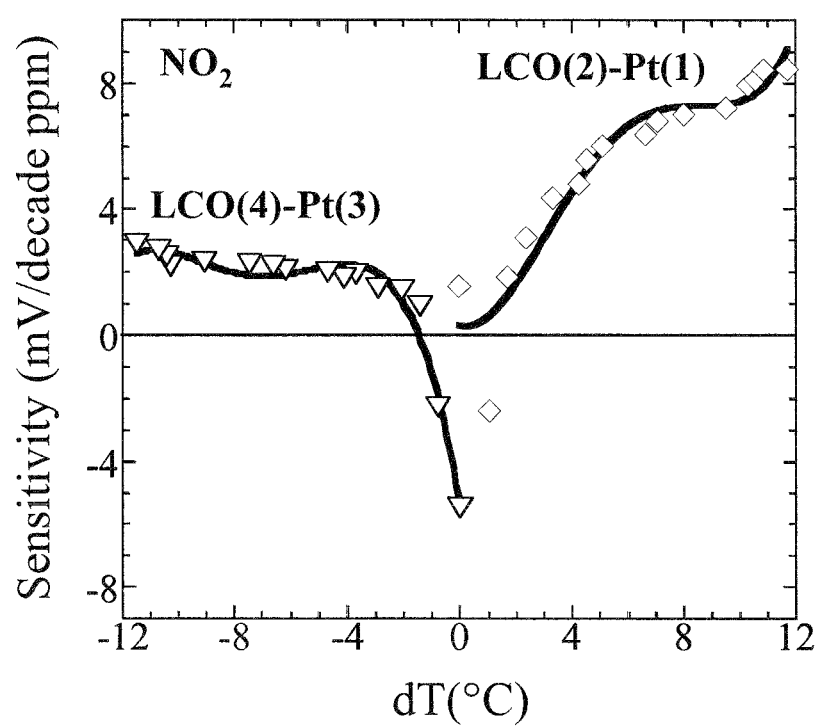
FIG. 16 shows the signal results from the LCO(4)-Pt(3) and LCO(2)-Pt(1) electrode-pairs, of the embodiment in FIGS. 7 and 8, in response to changes in gas concentration of $NO_2$.
Figure 17A:
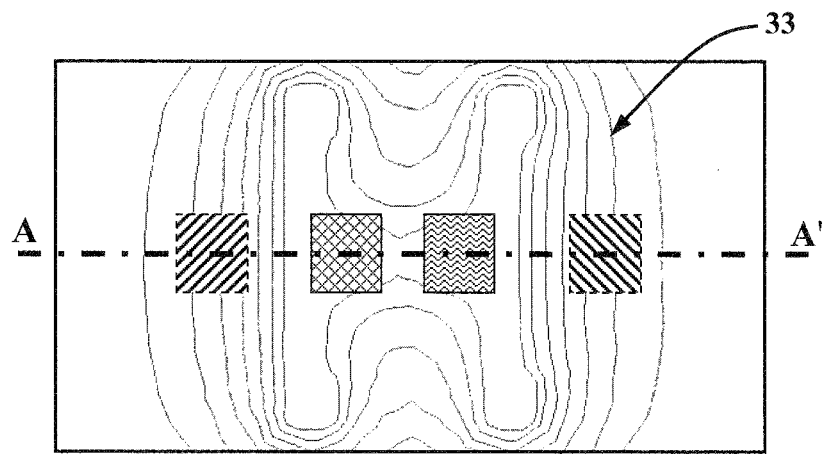
FIG. 17A shows the temperature contour plot for embodiment shown in FIGS. 7 and 8.
Figure 17B:
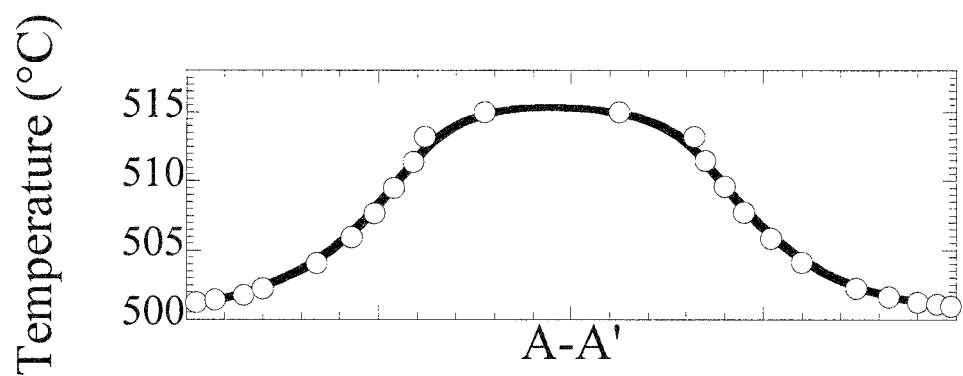
FIG. 17B shows the temperature profile through the cross-section of FIG. 17A.
Figure 18A:
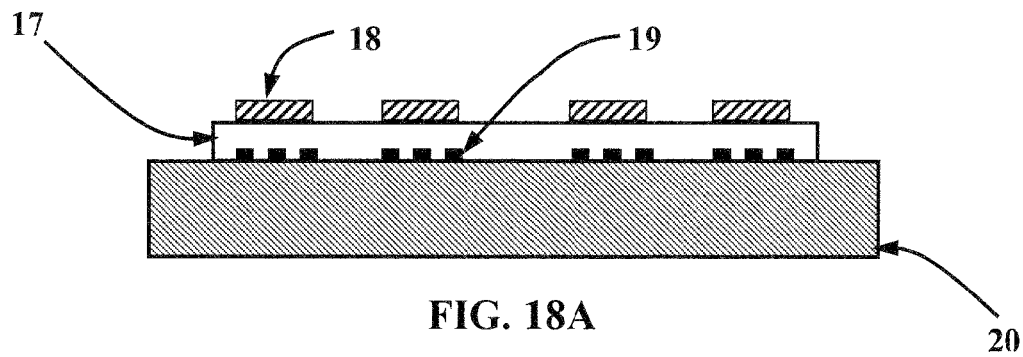
FIG. 18A shows an embodiment with structural support and electrolyte with embedded heaters and sensing electrodes deposited on top, where a multitude of electrode pairs may exist.
Figure 18B:
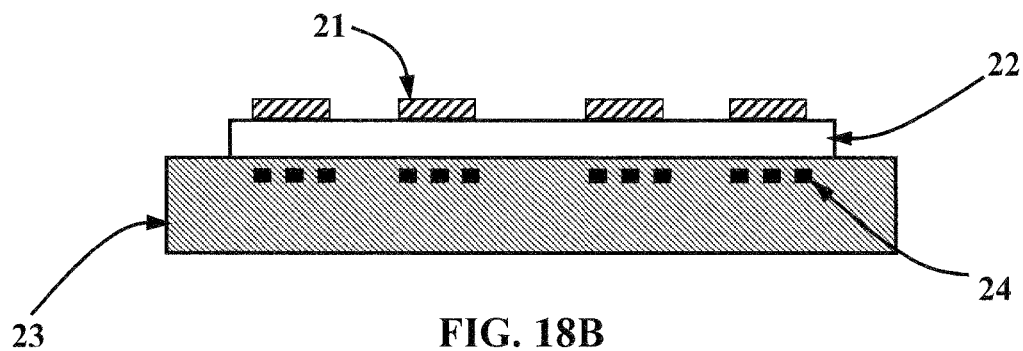
FIG. 18B shows an embodiment with structural support with embedded heaters and electrolyte and sensing electrodes deposited on top, where a multitude of electrode pairs may exist.
Figure 18C:
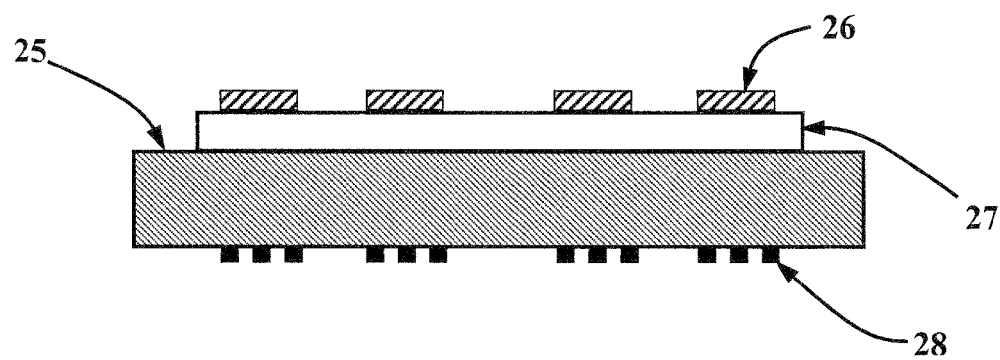
FIG. 18C shows an embodiment with structural support with backside heaters and topside deposited electrolyte and sensing electrodes, where a multitude of electrode pairs may exist.
Figure 18D:
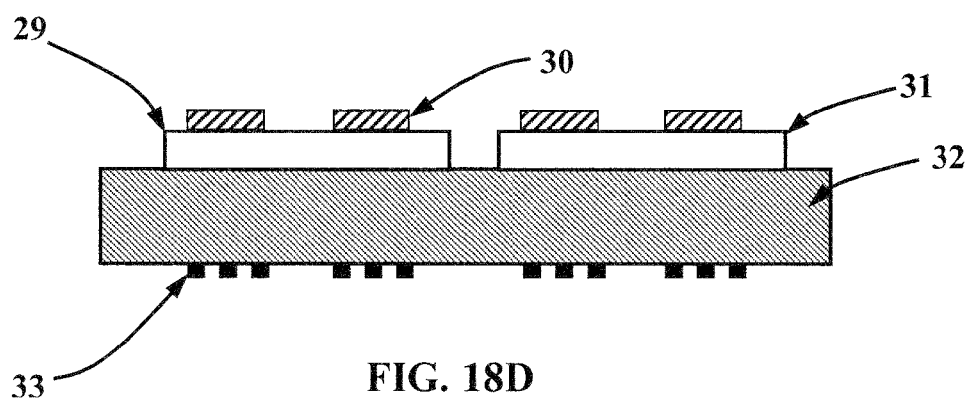
FIG. 18D shows an embodiment with structural support with backside heaters and separate electrolyte layers with sensing electrodes for different electrode-pairs, where a multitude of electrode pairs and electrolyte layers may exist.
Figure 19:
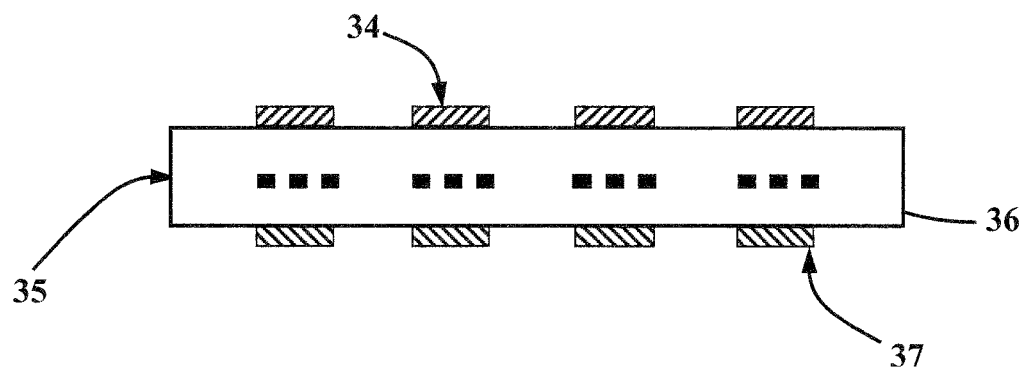
FIG. 19 shows an embodiment with an electrolyte support with embedded heaters, and sensing electrodes on opposite sides of the electrolyte, where a multitude of electrode pairs and electrolyte layers may exist.
Figure 20:
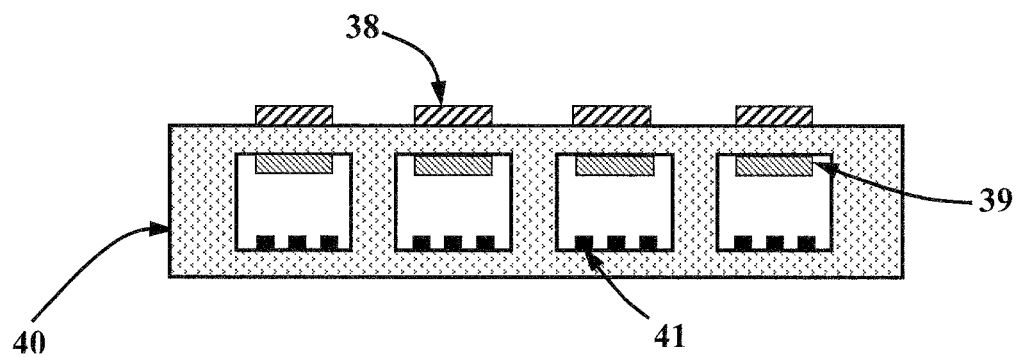
FIG. 20 shows an embodiment with one or more chambers inside the structural electrolyte, with heaters deposited on one side of the chamber, sensing electrodes are positioned on the other side, and additional sensing electrodes positioned on the outside of the structural electrolyte, where the chamber can be used for a reference gas.
Figure 21A:
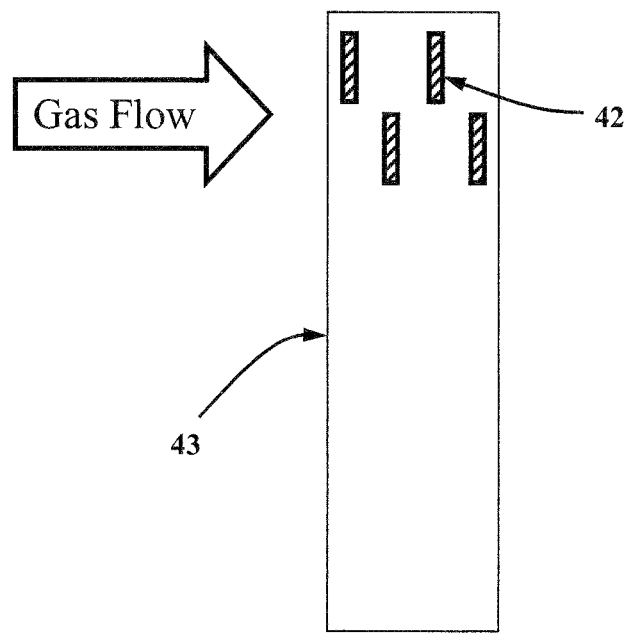
FIG. 21A shows an embodiment with sensing electrodes staggered and separated from each other on the top of the electrolyte and/or structural support.
Figure 21B:
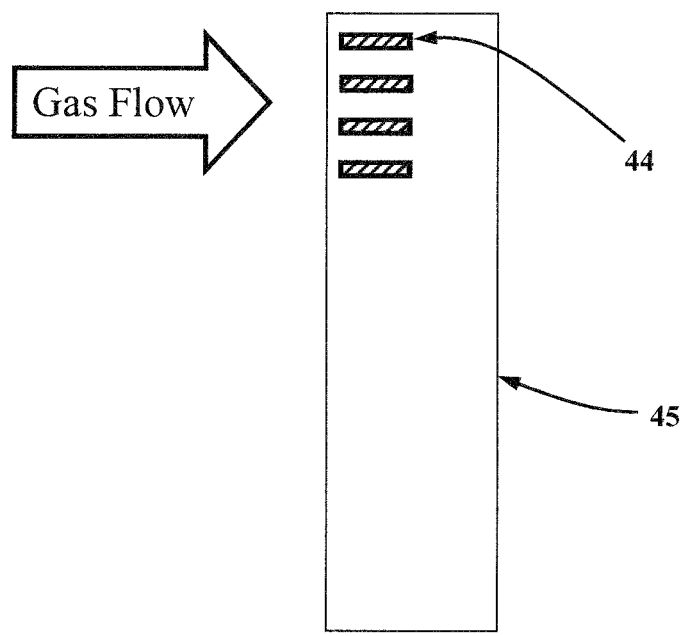
FIG. 21B shows an embodiment the sensing electrodes oriented in a different manner with respect to the gas flow direction.
Figure 22:
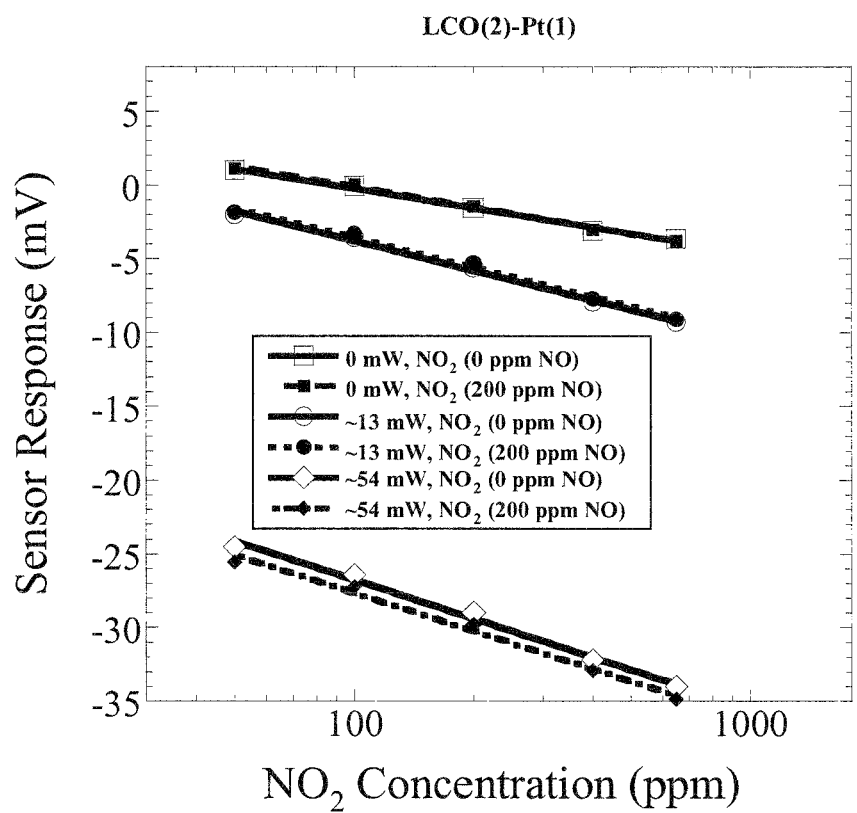
FIG. 22 shows a (log scale) plot of the sensor response to $NO_2$ for the LCO(2)-Pt(1) electrode-pair of the embodiment in FIGS. 7 and 8, tested at a higher ambient temperature than for FIGS. 9 to 16, for several different instances of total heater power, where conditions tested include gas steps of $NO_2$ with 0 ppm NO and 200 ppm NO gas mixtures.
Figure 23:
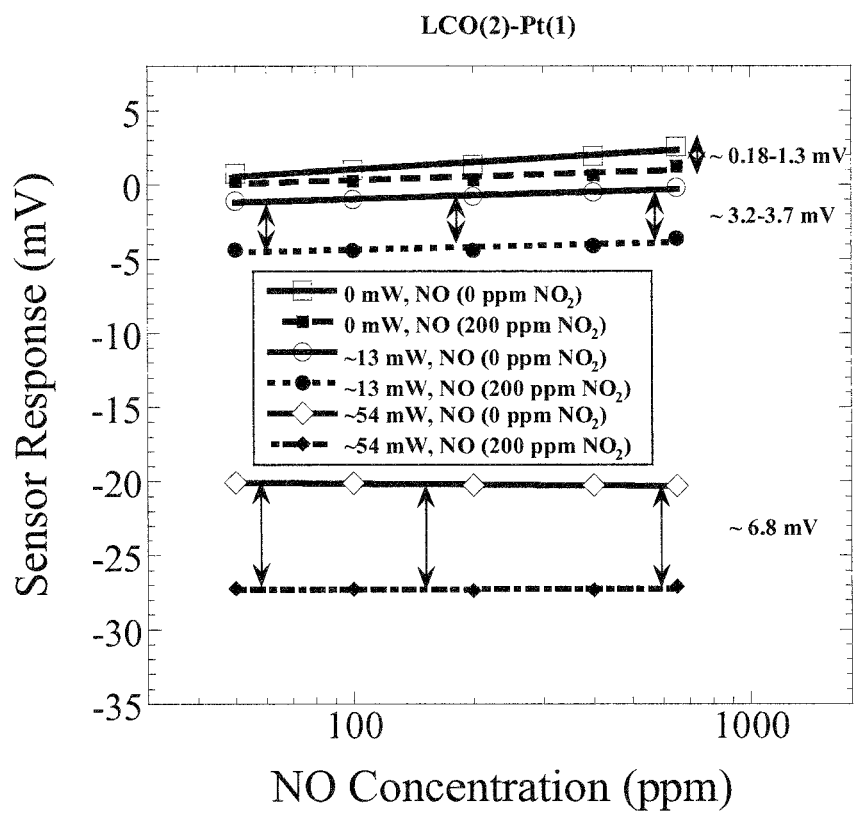
FIG. 23 shows a (log scale) plot of the sensor response to NO for the LCO(2)-Pt(1) electrode-pair of the embodiment in FIGS. 7 and 8, tested at a higher ambient temperature than for FIGS. 9 to 16, for several different instances of total heater power, where conditions tested include gas steps of NO with 0 ppm NO and 200 ppm $NO_2$ gas mixtures, where the shifts in response caused by introduction of $NO_2$ into the NO gas stream are also marked.

FIG. 7 shows another specific embodiment of the subject invention, and FIG. 8 shows a cross-sectional view of the same embodiment. The device includes two $La_2CuO_4$ electrodes and two Platinum electrodes, interdigitated with each other, on one side of a substrate. On the other side of the substrate, incorporating an electrolyte, are four Platinum electrodes, where the inner two are heaters and temperature sensors and the outer two are temperature sensors. This arrangement allows the two LCO electrodes to be maintained at different temperatures and the two Platinum sensing electrodes to be at different temperatures. If the two heated electrodes are maintained at constant temperatures, this allows six electrode-pair combinations for receiving signals. If the heated electrodes are designed to have more temperatures during operation, then more electrode-pair combinations can be created, with a specific electrode at two different temperatures acting as two electrodes for the purposes of providing output sensor signals. FIGS. 9-10 show sensor responses for NO and $NO_2$ for the electrode-pair having the non-heated LCO electrode and the heated Platinum electrode showing the results for increasing temperature difference and absolute temperature of each electrode. The slopes of the plots from FIGS. 9-10 can be taken, which represent the sensitivity (mV change in signal per decade change in gas concentration), to make trend plots provided in FIGS. 11-16. Each curve represents a different heater setpoint, which in turn represents a different temperature difference between the electrodes for the device shown in FIGS. 7-8. This was repeated for each of the six electrode signals from the four sensing electrodes for the device shown in FIGS. 7-8. In the trend plots the curve where |dT| is equal to zero is the case where the heaters were not being operated.

With respect to the device shown in FIGS. 7-8, more sensor signals can be measured than the number of sensing electrodes on the device itself. This is possible because some of the electrodes are at different temperatures. Furthermore, the device can have electrode-pairs that are selective to NO only and other electrode-pairs that are selective to $NO_2$ only. Other embodiments can have electrode pairs that are selective to other gases such as CO and $CO_2$. In fact, for some of the heater setpoints there were examples of the electrode-pairs switching their signal direction as they went either more positive or negative. This indicates that for a given electrode material or pair of materials, if the temperature is kept different between them, then the electrode-pair can be utilized in a way that results in it being sensitive or insensitive to one or more gases.

Furthermore, the sensors can take advantage of both changes in absolute temperature and differences in temperature between electrodes making up electrode-pairs. Sensitivity to a given species typically is altered at higher temperatures. If two sensing electrodes are brought above the temperature where they are no longer sensitive to one gas, but both are still sensitive to another gas, then the signal will be selective. Additionally, it is possible that if the temperature of one of the two electrodes is further increased that the signal, which is now selective, will also benefit from an increase in sensitivity as the individual potentials of the electrodes is further changed. This can be taken advantage of based on how the sensing electrodes' sensitivity changes with temperature and the specific gas species the electrodes are exposed to. In specific embodiments, pattern recognition is not used, thereby reducing device costs and improving sensor performance. The performance is also improved because one is able to increase the sensitivity of some of the electrode-pairs using the same methods for achieving differences in temperature between the electrodes. This can also be done by changes in microstructure and geometry of device.

The array of sensing electrodes used for various embodiments of the invention can include several different sensing electrodes. A reference or pseudo-reference electrode can be included, if desired. In embodiments, each sensing electrode can be used to make up a "sensing electrode-pair." Furthermore, each sensing electrode can be used in combination with other sensing electrodes in the array to make up multiple electrode-pairs. Different electrode configurations or properties will change the way in which the sensor performs. This allows specific tailoring of the device to achieve the desired performance (e.g., sensitivity, selectivity, and response time) for specific applications.

Depending on the specific design and/or application, the sensing electrodes can be configured using the same or different electrode materials, using the same and/or different microstructures, using the same and/or different geometries (shape and thickness), and/or being operated at the same and/or different temperatures. The key is that the two electrodes to be used to create a sensing electrode-pair, when an electrolyte is in contact with the two electrodes, should create a voltage potential across the sensing electrode-pair when exposed to a gas species to be measured or to a mixture of gases which includes a gas species to be measured. By having the two electrodes have some combination of different microstructures, different geometries (shape and thickness), different materials, being at different temperatures, and/or any other alteration which causes the materials to differ in some way, the conditions to create a sensing electrode-pair can exist.

Temperature control of the sensing electrodes can be used to achieve the desired performance. Depending on the sensing electrode-pair, the performance of the measured signal can generally be modified via thermal modification. Furthermore, the temperature is preferably kept from changing due to external sources (such as changes in the gas stream temperature). Therefore, embodiments of the device can incorporate a means to monitor the temperature of the sensing electrodes and a means to change their temperatures when needed.

Heating elements can be utilized to modify the temperature of the sensing electrodes when needed. The heating elements can be on the opposite side of a substrate from the sensing electrodes, each appropriately aligned with a specific sensing electrode. Heating elements can be located on the same side of the substrate as the sensing electrodes as well. Heating elements may also be embedded in or on the electrolyte or support. Different heating element patterns can be implemented (e.g., C-shaped, spiral, or serpentine patterns) in order to yield the ideal thermal distribution on the device. The heat can be generated by Joule heating (Heat=Power*Time=Current$^2$*Resistance*Time). The heating current may be voltage or current controlled and delivered in pulses or in a constant manner. The heating current may be delivered by simple current splitting or by individual (current or voltage) output to the heating elements.

The temperature of the sensing electrodes can also be controlled via cooling, either in conjunction with heating or alone. In an embodiment, cooling can be accomplished using a method known as thermoelectric cooling, for example, using a solid-state heat pump. Cooling can also be accomplished with the use of heat sinks. By changing the temperature on other areas of the device, a temperature under a sensing electrode may also be lowered. Other designs to accomplish cooling of specific regions of the device are also possible.

Temperature monitoring can be accomplished by measuring the resistance or other temperature related parameter of elements made of metal, semiconductor, or other material that cover an area under or near the sensing electrodes. Temperature sensors also may be embedded or lay exposed on the surface. Multiple methods of temperature sensing are possible including use of RTDs and thermocouples. Temperature sensors may act simultaneously as heating elements or may be stand alone elements. Temperature sensors may act simultaneously as cooling or heating elements as well.

There are several different signals that may be monitored. Some of the various signals that can be monitored include the voltage of sensing electrodes and/or voltage differences of sensing electrode-pairs. Multiplexing can be used to monitor the multiple voltage signals from the corresponding multiple sensing electrode-pairs. Resistance or other parameter monitoring of temperature sensors can also be accomplished and can also utilize multiplexing.

Various embodiments incorporate a detector for measuring an electrical characteristic with respect to the sensing electrode. One method of detection in the sensor array may be potentiometric. The array may include other methods of detection such as conductimetric (or impedancemetric), capacitive, or other methods for detecting gas species. This extension of the sensor array can be achieved monolithically or on separate substrates connected to a common measurement system.

There are numerous techniques that can be employed in the manufacture of embodiments of the subject devices. Multiple devices may be made simultaneously and separated by various means after manufacture. Any combination of the following techniques can be utilized. Multilayer fabrication, such as tape-casting, and/or screen-printing, can be used. Bottom-Up (additive) approach, such as direct-write methods (e.g., pump- or aerosol-based deposition), laser micromachining, and/or laser sintering, can be used. Multi-step (subtractive) approach, such as microfabrication using photolithography and other techniques used in the fabrication of microelectronics and microelectro-mechanical systems (MEMS), and/or electron-beam and laser-based subtractive fabrication, can be used. Wire attachment methods and metallization, such as metals used for metallization or wire attachment must be able to withstand harsh environments. Wire bonding (e.g., Au or Pt wire), brazing, and/or other methods of wire attachment can be used. Different metallization (materials or otherwise) may exist in multiple layers and connected to each other by vias that exist in between layers or on the outside of the device. Device packaging can be accomplished via standard or other packaging techniques. Designs of high-temperature (or any other) electronics and/or sensors may be used with this device. These may be incorporated into the sensor for a monolithic device or exist as a part of a hybrid system.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A gas sensor, comprising:
   a substrate, wherein the substrate comprises an electrolyte;
   a reference electrode;
   at least two sensing electrodes, wherein the at least two sensing electrodes are positioned on the substrate, wherein the at least two sensing electrodes are in contact with the electrolyte;
   a temperature control mechanism, wherein the temperature control mechanism is configured to alter a corresponding one or more temperatures of one or more of the at least two sensing electrodes such that the at least two sensing electrodes are at a corresponding at least two operating temperatures; and
   an EMF detector, wherein the EMF detector is configured to measure a corresponding at least two EMFs between the at least two sensing electrodes and the reference to produce a corresponding at least two measured EMFs,
   wherein the gas sensor is configured such that, when the at least two sensing electrodes are at the corresponding at least two operating temperatures, the reference electrode is at a reference electrode temperature, and the at least two sensing electrodes are exposed to an environment of interest, the at least two measured EMFs provide information with respect to one or more gases in the environment of interest.

2. The gas sensor according to claim 1, wherein the at least two sensing electrodes are disposed on a surface of the substrate.

3. The gas sensor according to claim 1, wherein a first measured EMF of the at least two measured EMFs between a first sensing electrode of the at least two sensing electrodes and the reference electrode indicates whether a first gas is present in the environment of interest.

4. The gas sensor according to claim 1, wherein a first measured EMF of the at least two measured EMFs between a first sensing electrode of the at least two sensing electrodes and the reference electrode indicates a concentration of a first gas present in the environment of interest.

5. The gas sensor according to claim 1, wherein the reference electrode is in contact with the electrolyte.

6. The gas sensor according to claim 5, wherein the reference electrode is exposed to the environment of interest, wherein the EMF detector is configured to measure an additional EMF between a first sensing electrode of the at least two sensing electrodes and a second sensing electrode of the at least two sensing electrodes to produce an additional measured EMF, wherein the gas sensor is configured such that, when the at least two sensing electrodes are at the corresponding at least two operating temperatures, the reference electrode is at a reference electrode temperature, and the at least two sensing electrodes are exposed to an environment of interest, the at least two measured EMFs and the additional measured EMF provide information with respect to one or more gases in the environment of interest.

7. The gas sensor according to claim 6, wherein upon exposure to a gas to be measured, a corresponding EMF occurs between a selected two sensing electrodes of the at least two sensing electrodes.

8. The gas sensor according to claim 6, wherein the first sensing electrode and the second sensing electrode are formed of the same material and are maintained at different temperatures by a corresponding first heating element and a corresponding second heating element.

9. The gas sensor according to claim 8, wherein the at least two sensing electrodes are all formed of the same material and are all maintained at different temperatures.

10. The gas sensor according to claim 8, wherein each of the at least one of the at least two sensing electrodes are formed of the same material, are maintained at the same temperature, and have different microstructures, sizes, or thicknesses than each of the other of the at least one of the at least two sensing electrodes of the same material.

11. The gas sensor according to claim 10, wherein the EMF detector is configured to measure a corresponding EMF of any two of the at least two sensing electrodes and the reference electrode maintained at a different temperature, having a different microstructure, having a different size, or having a different thickness.

12. The gas sensor according to claim 6, wherein the at least two sensing electrodes and the reference electrode comprise one or more electrodes of a first material and one or more electrodes of a second material, wherein each of the electrodes of the at least two sensing electrodes and reference electrode is maintained at one of two or more different temperatures by two or more heating elements.

13. The gas sensor according to claim 12, wherein the EMF detector is configured to measure a corresponding EMF of any two electrodes of the at least two sensing electrodes and reference electrode formed of a different material or maintained at a different temperature.

14. The gas sensor according to claim 12, wherein each of the at least one of the at least two sensing electrodes and reference electrode formed of a same material are maintained at a first of the two or more temperatures and have different microstructures, sizes, or thicknesses than each of the other of the at least one of the at least two sensing electrodes of the same material.

15. The gas sensor according to claim 14, wherein any two electrodes of the at least two sensing electrodes and reference electrode are formed of a different material, maintained at a different temperature, have a different microstructure, have a different size, or have a different thickness.

16. The gas sensor according to claim 12, wherein the heating elements comprises resistor elements.

17. The gas sensor according to claim 16, wherein the resistor elements are formed of platinum.

18. The gas sensor according to claim 16, wherein each resistor element is disposed in a pattern on an opposite surface of the electrolyte to one of the sensing electrodes of the at least two sensing electrodes and reference electrode.

19. The gas sensor according to claim 16, wherein a pattern of each resistor element comprises a C-shape pattern, a spiral pattern, or a serpentine pattern.

20. The gas sensor according to claim 6, wherein electrodes of the at least two sensing electrodes and reference electrode comprise metal or a semiconducting oxide.

21. The gas sensor according to claim 6, wherein electrodes of the at least two sensing electrodes and reference electrode comprise at least one platinum electrode.

22. The gas sensor according to claim 6, wherein electrodes of the at least two sensing electrodes and reference electrode comprise at least one $La_2CuO_4$ (LCO) electrode.

23. The gas sensor according to claim 6, wherein the first sensing electrode and the second sensing electrode provide the additional measured EMF providing information with respect to a first of the one or more gases and a third sensing electrode and a fourth sensing electrode provide a second additional measured EMF providing information with respect to a second of the one or more gases.

24. The gas sensor according to claim 23, wherein the first of the one or more gases is NO and the second of the one or more gases is $NO_2$.

25. The gas sensor according to claim 6, wherein the first sensing electrode and the second sensing electrode provide the additional measured EMF providing information with respect to a first of the one or more gases and a third sensing electrode and a fourth sensing electrode provide a second additional measured EMF providing information with respect to the first of the one or more gases and a second of the one or more gases.

26. The gas sensor according to claim 25, wherein the first of the one or more gases is $NO_2$ and the second of the one or more gases is NO.

27. The gas sensor according to claim 26, wherein the information with respect to the first of the one or more gases and the second of the one or more gases is a sum of a concentration of NO and a concentration of $NO_2$.

28. The gas sensor according to claim 5, wherein the reference electrode is exposed to the environment of interest, wherein the reference electrode has a different shape than the one or more of the at least two sensing electrodes.

29. The gas sensor according to claim 5, wherein the reference electrode is exposed to the environment of interest, wherein the reference electrode temperature is different than the one or more operating temperatures of the one or more of the at least two sensing electrodes.

30. The gas sensor according to claim 5, wherein the reference electrode is exposed to the environment of interest, wherein the reference electrode is made of a different material than the one or more of the at least two sensing electrodes.

31. The gas sensor according to claim 5, wherein the reference electrode is exposed to the environment of interest, wherein the reference electrode comprises a different microstructure than the one or more of the at least two sensing electrodes.

32. The gas sensor according to claim 1, wherein the temperature control mechanism comprises at least one heater.

33. The gas sensor according to claim 32, wherein the at least one heater is in thermal contact with the electrolyte.

34. The gas sensor according to claim 32, wherein the at least one heater is detached from the electrolyte and the one or more of the at least two sensing electrodes.

35. The gas sensor according to claim 32, wherein the at least one heater radiatively heats the one or more of the at least two sensing electrodes.

36. The gas sensor according to claim 32, wherein the at least one heater conductively heats the one or more of the at least two sensing electrodes.

37. The gas sensor according to claim 32, wherein the at least one heater comprises the one or more of the at least two sensing electrodes and at least one current source for driving the one or more of the at least two sensing electrodes with a corresponding one or more current.

38. The gas sensor according to claim 32, wherein the at least one heater comprises a corresponding one or more heating elements, wherein when a corresponding one or more heating currents are passed through the one or more heating elements the one or more heating elements produces heat that heats the one or more of the at least two sensing electrodes.

39. The gas sensor according to claim 1, wherein the temperature control mechanism is configured to cool the one or more of the at least two sensing electrodes.

40. The gas sensor according to claim 1, further comprising:
a corresponding one or more temperature sensors, wherein the one or more temperature sensors measure a corresponding one or more temperatures of the one or more of the at least two sensing electrodes.

41. The gas sensor according to claim 1, wherein the at least two sensing electrodes are made of a semiconductor.

42. The gas sensor according to claim 41, wherein the semiconductor is a metal oxide or metal oxide compound.

43. The gas sensor according to claim 42, wherein the semiconductor comprises one or more of the following: $SnO_2$, $TiO_2$, TYPd5, $MoO_3$, $ZnMoO_4$ (ZM), $WO_3$, $La_2CuO_4$, and mixtures thereof.

44. The gas sensor according to claim 1, wherein the at least two sensing electrodes are made of a metal.

45. The gas sensor according to claim 1, wherein the electrolyte is an oxygen ion-conducting electrolyte.

46. The gas sensor according to claim 45, wherein the electrolyte is based on $ZrO_2$, $Bi_2O_3$, or $CeO_2$.

47. The gas sensor according to claim 1, wherein the one or more gases are one or more of $NO_x$, $CO_x$, and $SO_x$.

48. The gas sensor according to claim 1, wherein the one or more gases is NO.

49. The gas sensor according to claim 1, wherein the one or more gases is $NO_2$.

50. The gas sensor according to claim 1, wherein the one or more gases are NO and $NO_2$.

51. The gas sensor according to claim 1,
wherein the at least two sensing electrodes are a first sensing electrode and a second sensing electrode, wherein the temperature control mechanism is a first heater and a second heater, wherein the first heater is configured to control a first temperature of the first sensing electrode, wherein the second heater is configured to control a second temperature of the second sensing electrode.

52. A gas sensor, comprising:
a substrate, wherein the substrate comprises an electrolyte;
at least two sensing electrodes, in contact with an electrolyte;
a temperature control mechanism, wherein the temperature control mechanism is configured to alter a corresponding one or more temperatures of one or more of the at least two sensing electrodes such that the at least two sensing electrodes are at a corresponding at least two operating temperatures; and
an impedance detector, wherein the impedance detector is configured to measure a corresponding at least two impedances of the at least two sensing electrodes to produce a corresponding at least two measured impedances, wherein the gas sensor is configured such that when the at least two sensing electrodes are at the corresponding at least two operating temperatures and the at least two sensing electrodes are exposed to an environment of interest, at least two measured impedances provide information with respect to one or more gases in the environment of interest.

53. A gas sensor, comprising:
a substrate wherein the substrate comprises an electrolyte;
at least two sensing electrodes, wherein the at least two sensing electrodes are positioned on the substrate, wherein the at least two sensing electrodes are in contact with the electrolyte;
a temperature control mechanism, wherein the temperature control mechanism is configured to alter a corresponding one or more temperatures of one or more of the at least two sensing electrodes such that the at least two sensing electrodes are at a corresponding at least two operating temperatures; and
a current detector, wherein the current detector is configured to measure a corresponding at least two currents in the at least two sensing electrodes to produce a corresponding at least two measured currents, wherein when the at least two sensing electrodes are at the corresponding at least two operating temperatures and the at least two sensing electrodes are exposed to an environment of interest the at least two measured currents provide information with respect to one or more gases in the environment of interest.

54. A method of sensing one or more gases, comprising:
providing a gas sensor, wherein the gas sensor comprises:
a substrate, wherein the substrate comprises an electrolyte;
a reference electrode;
at least two sensing electrodes, wherein the at least two sensing electrodes are positioned on the substrate, wherein the at least two sensing electrodes are in contact with the electrolyte;
a temperature control mechanism, wherein the temperature control mechanism is configured to alter a corresponding one or more temperatures of one or more of the at least two sensing electrodes such that the at least two sensing electrodes are at a corresponding at least two operating temperatures; and
an EMF detector, wherein the EMF detector is configured to measure a corresponding at least two EMFs between the at least two sensing electrodes and the reference to produce a corresponding at least two measured EMFs,
wherein the gas sensor is configured such that, when the at least two sensing electrodes are at the corresponding at least two operating temperatures, the reference electrode is at a reference electrode temperature, and the at least two sensing electrodes are exposed to an environment of interest, the at least two measured EMFs provide information with respect to one or more gases in the environment of interest,
exposing the at least two sensing electrodes to an environment of interest;
altering the one or more temperatures of the one or more of the at least two sensing electrodes such that the at least two sensing electrodes are at a corresponding at least two operating temperatures; and
measuring a corresponding at least two EMFs between the at least two sensing electrodes and the reference electrode to produce a corresponding at least two measured EMFs, wherein the at least two measured EMFs provide information with respect to one or more gases in the environment of interest.

* * * * *

UNITED STATES PATENT AND TRADEMARK OFFICE
CERTIFICATE OF CORRECTION

Page 1 of 2

PATENT NO. : 9,027,387 B2
APPLICATION NO. : 12/682365
DATED : May 12, 2015
INVENTOR(S) : Bryan M. Blackburn and Eric D. Wachsman It is certified that error appears in the above-identified patent and that said Letters Patent is hereby corrected as shown below:

In the specification,

Column 1,
line 54, "the selectivity and cross-sensitivity of these sensors is currently" should read
--the selectivity and cross-sensitivity of these sensors are currently--

Column 2,
line 18, "on or more gases" should read --one or more gases--

Column 4,
line 25, "temperature determining technique" should read --temperature determining techniques--

Column 7,
line 39, "36 embedded in side." should read --36 embedded inside.--

Column 8,
line 6, "temperatures sensors" should read --temperature sensors--

Figure 24:
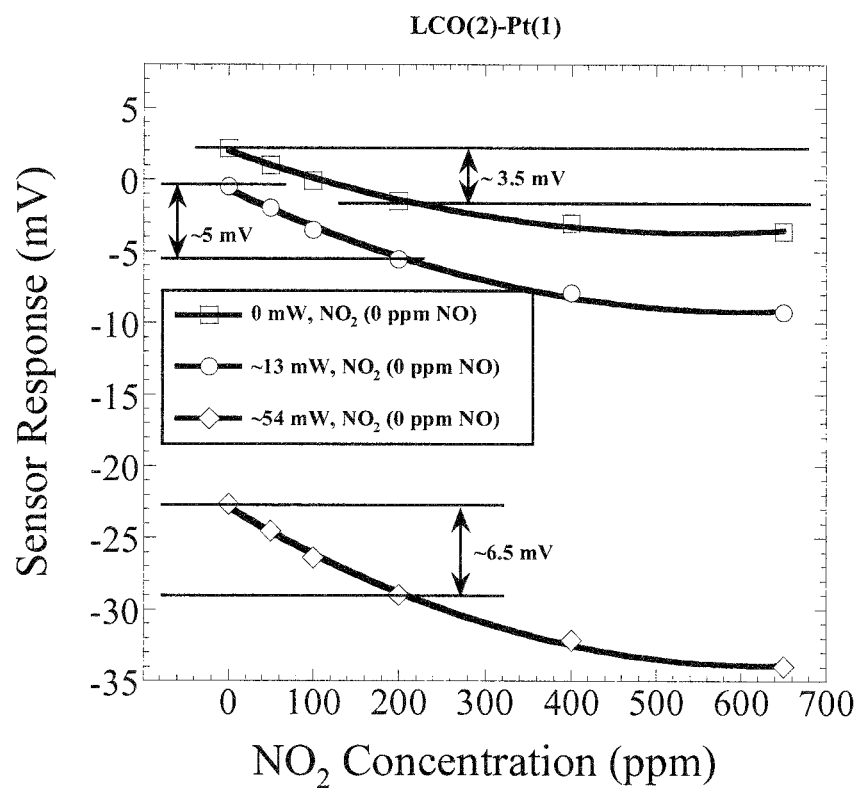
FIG. 24 shows a (linear scale) plot of FIG. 22, for the embodiment in FIGS. 7 and 8, with the voltage change from 0 to 200 ppm $NO_2$ marked for each heater power condition.
Figure 25:
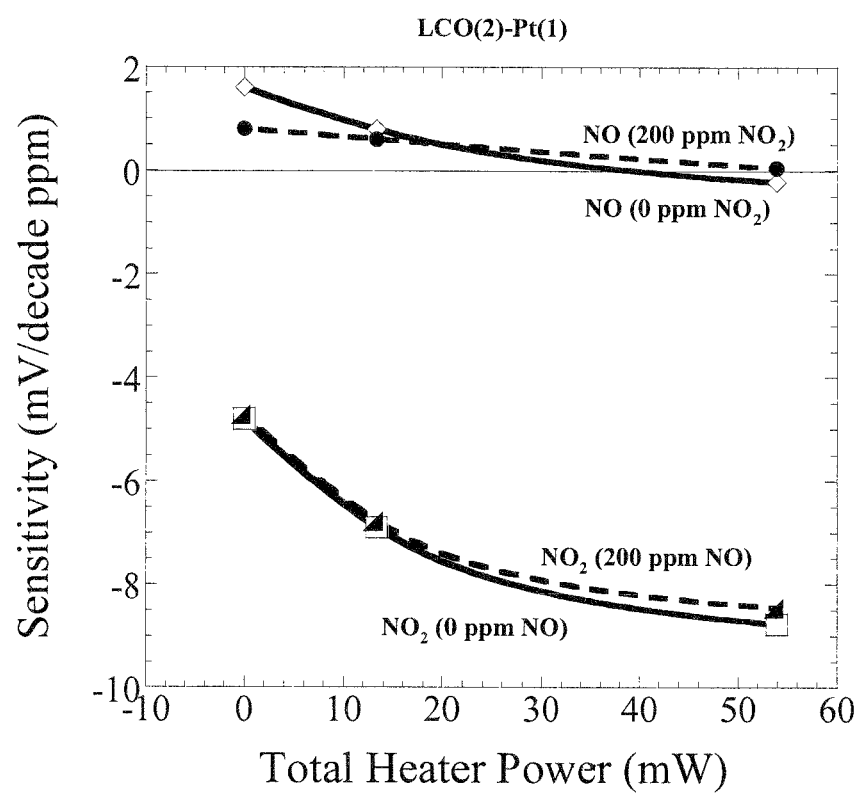
FIG. 25 shows sensitivity versus total heater power for the LCO(2)-Pt(1) electrode-pair, for the embodiment in FIGS. 7 and 8, taken from FIGS. 22 and 23.
Figure 26:
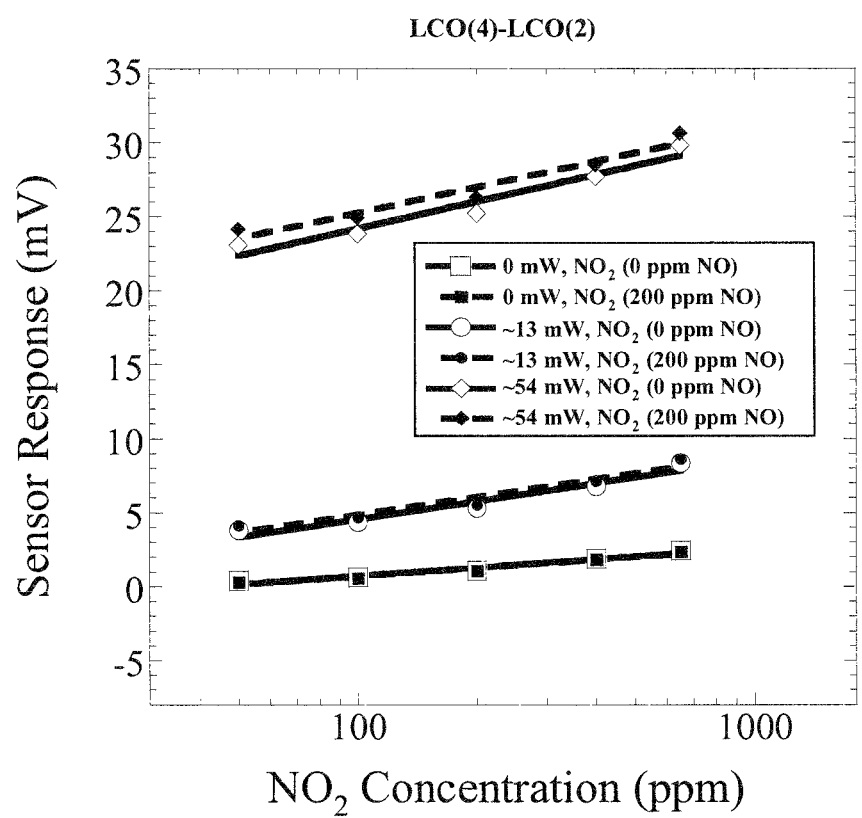
FIG. 26 shows the NO response of the LCO(4)-LCO(2) electrode-pair of the embodiment in FIGS. 7 and 8, tested at a higher ambient temperature than for FIGS. 9 to 16, for several different instances of total heater power.
Figure 27:
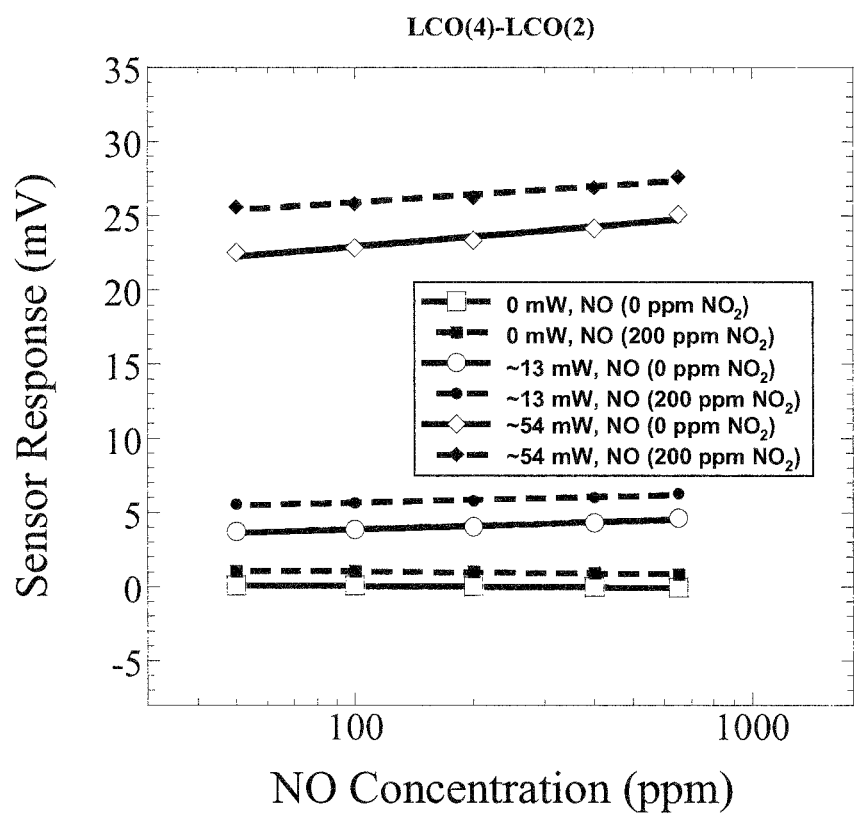
FIG. 27 shows the $NO_2$ response of the LCO(4)-LCO(2) electrode-pair of the embodiment in FIGS. 7 and 8, tested at a higher ambient temperature than for FIGS. 9 to 16, for several different instances of total heater power.
Figure 28:
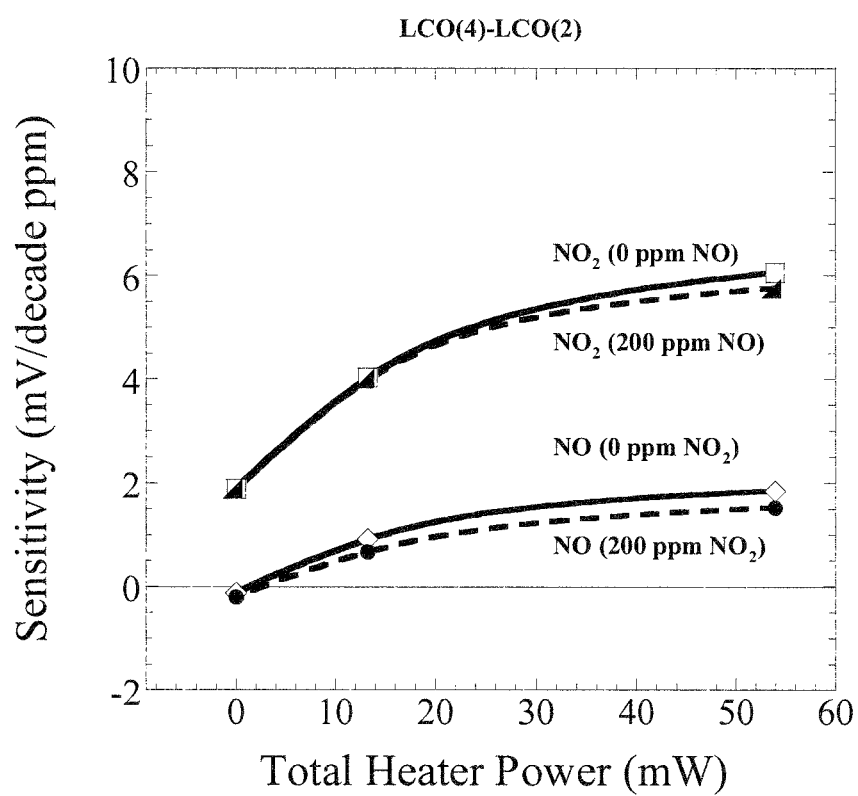
FIG. 28 shows the sensitivity versus total heater power for the LCO(4)-LCO(2) electrode-pair, for the embodiment in FIGS. 7 and 8, taken from FIGS. 26 and 27.
Figure 29:
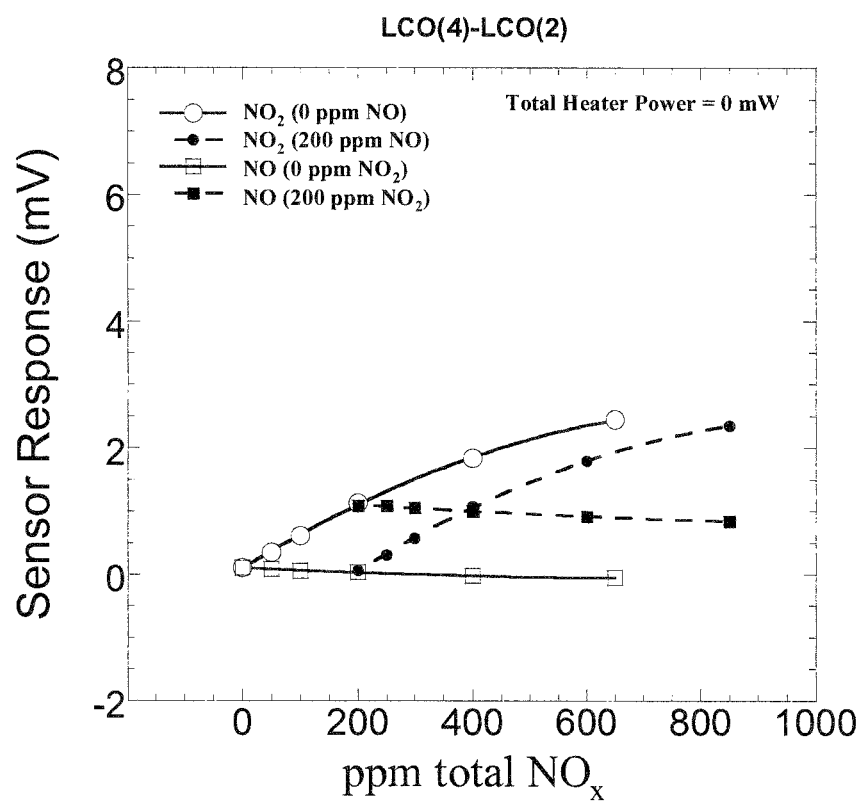
FIG. 29 demonstrates the total $NO_x$ sensing capability of the LCO(4)-LCO(2) electrode-pair, for the embodiment in FIGS. 7 and 8, without the use of the heaters (i.e., total heater power is 0 mW).
Figure 30:
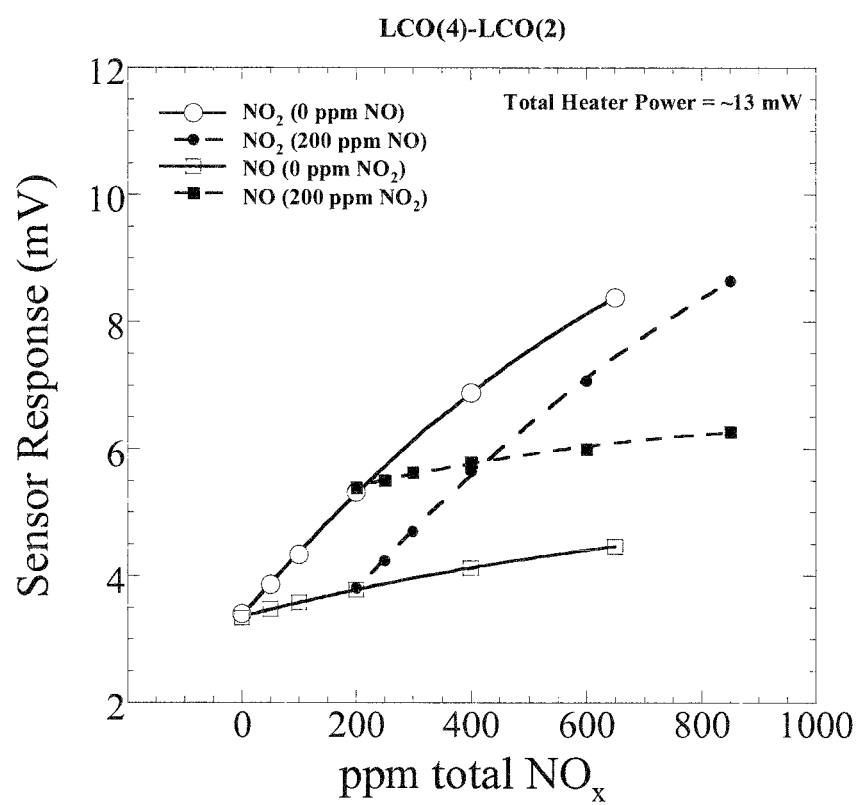
FIG. 30 demonstrates the total $NO_x$ sensing capability of the LCO(4)-LCO(2) electrode-pair, for the embodiment in FIGS. 7 and 8, for a total heater power of 13 mW.
Figure 31:
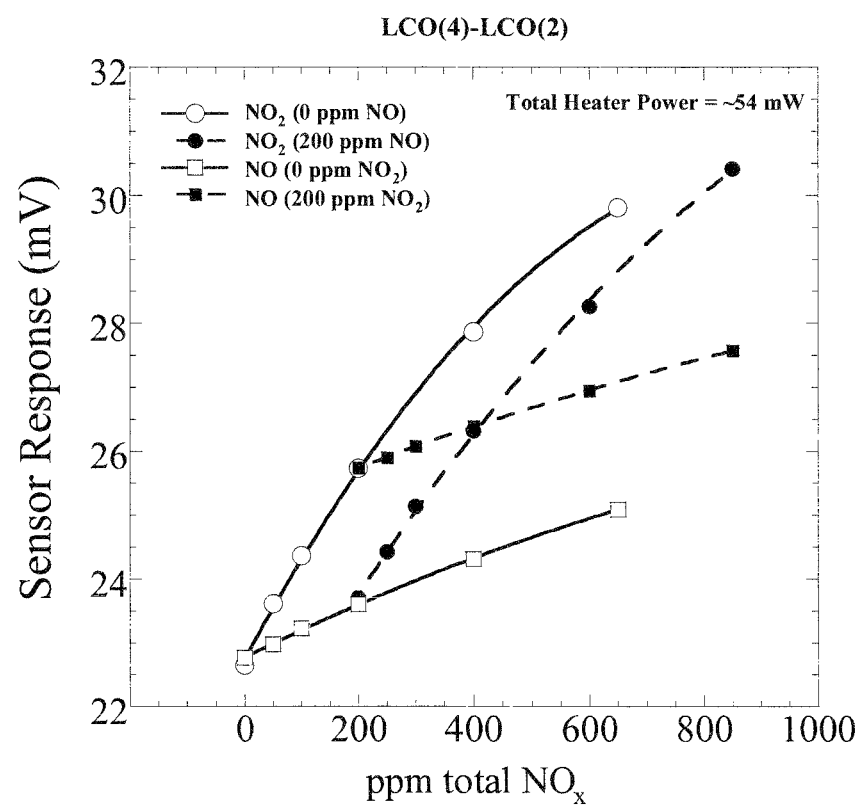
FIG. 31 demonstrates the total $NO_x$ sensing capability of the LCO(4)-LCO(2) electrode-pair, for the embodiment in FIGS. 7 and 8, for a total heater power of 54 mW.

Column 8,
line 54, "Also marked in FIG. 24, are the difference" should read --Also marked in Figure 24 is the difference--

Column 9,
line 44, "to detect total NO concentrations" should read --to detect total $NO_x$ concentrations--

Column 10,
line 4, "total ppm NO in" should read --total ppm $NO_x$ in--

Signed and Sealed this
Twenty-third Day of February, 2016

Michelle K. Lee
*Director of the United States Patent and Trademark Office*

Column 10,
line 18, "a total NO concentration" should read --a total $No_x$ concentration--

Column 10,
line 24, "the total NO" should read --the total $NO_x$--

Column 10,
line 31, "over NO in NO gas mixtures" should read --over NO in $NO_x$ gas mixtures--

Column 11,
line 2, "temperatures difference" should read --temperature difference--

Column 12,
line 44, "sensing on or more gases" should read --sensing one or more gases--

Column 12,
line 46, "sensing on or more gases" should read --sensing one or more gases--

Column 12,
line 48, "sensors and method" should read --sensors and methods--

Column 13,
line 39, "results of from this device" should read --results from this device--

Column 13,
line 56, "selectivity that changes" should read --selectivity changes--

Column 14,
line 2, "temperature, one" should read --temperature, and one--

Column 17,
line 14, "potentials of the electrodes is further changed" should read --potentials of the electrodes are further changed--

Column 18,
line 2, "electrolyte or support" should read --electrolyte for support--

In the claims,

Column 20,
line 55, "elements comprises resistor elements" should read --elements comprise resistor elements--